(12) United States Patent
Benner

(10) Patent No.: US 6,617,106 B1
(45) Date of Patent: *Sep. 9, 2003

(54) METHODS FOR PREPARING OLIGONUCLEOTIDES CONTAINING NON-STANDARD NUCLEOTIDES

(76) Inventor: Steven Albert Benner, 1501 NW. 68th Ter., Gainesville, FL (US) 32605

( * ) Notice: Subject to any disclaimer, the term of this patent is extended or adjusted under 35 U.S.C. 154(b) by 0 days.

This patent is subject to a terminal disclaimer.

(21) Appl. No.: 09/538,338

(22) Filed: Mar. 29, 2000

Related U.S. Application Data

(63) Continuation of application No. 08/775,401, filed on Dec. 31, 1996, now Pat. No. 6,140,496, which is a continuation-in-part of application No. 08/542,142, filed on Oct. 12, 1995, now Pat. No. 6,037,120, and a continuation-in-part of application No. 08/375,132, filed on Jan. 17, 1995, now Pat. No. 6,001,983, which is a continuation-in-part of application No. 07/594,290, filed on Oct. 9, 1990, now Pat. No. 5,432,272.

(51) Int. Cl.[7] ............................ C12Q 1/68; C12P 19/34; C07H 21/00; C07H 21/02; C07H 21/04
(52) U.S. Cl. ................... 435/6; 435/91.1; 435/91.5; 536/23.1; 536/25.3; 536/25.32
(58) Field of Search .................... 435/6, 91.1, 91.5; 536/23.1, 25.3, 25.32, 25.33, 25.34

(56) References Cited

U.S. PATENT DOCUMENTS

| | | | |
|---|---|---|---|
| 5,177,064 A | | 1/1993 | Bodor .................... 564/399 |
| 5,412,088 A | | 5/1995 | Jones et al. ............. 536/27.81 |
| 5,432,272 A | * | 7/1995 | Benner .................... 536/25.3 |
| 5,470,974 A | | 11/1995 | Summerton et al. ........ 544/118 |
| 6,001,983 A | * | 12/1999 | Benner .................... 536/23.1 |
| 6,037,120 A | * | 3/2000 | Benner ...................... 435/6 |

OTHER PUBLICATIONS

Tor et al. (1993) J. Am Chem Soc. 115: 4461–4467.*
Piccirilli et al. (1991) Biochemistry 30: 10350–10356.*
Bain, J.D. et al., *J. Am. Chem. Soc.*, vol. 111, pp. 8014–8014 (1989).
Been, M.D. et al., *Science*, vol. 239, pp. 1412–1416 (1988).
Cech, T. et al., *Ann. Rev. Biochem*, vol. 55, pp. 599–629 (1986).
Chen, J. et al., *Biochemistry*, vol. 27, pp. 6032–6038 (1988).
Chu, C.K. et al., *J. Org. Chem.*, vol. 42, No. 4, pp. 711–714 (1977).
Cobianchi, F. et al., *Methods in Enzymology*, vol. 152, pp. 94–110 (1987).
Eritia et al., *Nucl. Acids. Res.*, vol. 14, No. 20, pp. 8135–8153 (1986).
Froehler, B.C. et al., *Nucl. Acids. Res.*, vol. 11, No. 22, pp. 8031–8036 (1983).
Golas et al., *Int. J. Biochem*, vol. 65, pp. 183–192 (1976).
Haseloff et al., *Nature*, vol. 334, pp. 585–591 (1988).
Kimura, J. et al., *Bull. Chem. Soc. Jpn*, vol. 53, pp. 3670–3677 (1980).

(List continued on next page.)

*Primary Examiner*—Jehanne Souaya
(74) *Attorney, Agent, or Firm*—Gregory T. Pletta

(57) ABSTRACT

The disclosure describes building blocks for preparing oligonucleotides carrying non-standard nucleobases that can pair with complementary non-standard nucleobases so as to fit the Watson-Crick geometry, in that the resulting base pair joins a monocyclic six membered ring pairing with a fused bicyclic heterocyclic ring system composed of a five member ring fused with a six membered ring, with the orientation of the heterocycles with respect to each other and with respect to the backbone chain analogous to that found in DNA and RNA, but with a pattern of hydrogen bonds holding the base pair together different from that found in the AT and GC base pairs (a "non-standard base pair").

4 Claims, 3 Drawing Sheets

OTHER PUBLICATIONS

Krosigk et al., *J. Am. Chem. Soc.*, vol. 117, pp. 5361–5362 (1995).

Langer, P.R. et al., *PNAS*, vol. 78, No. 11, pp. 6633–6637 (1981).

Larson, K. et al., *Mutation Res.*, vol. 150, pp. 77–84 (1985).

Leary, J.J. et al., *PNAS*, vol. 80, pp. 4045–4049 (1983).

Mantsch, H.H. et al., *Biochem.*, vol. 14, No. 26, pp. 5593–5601 (1975).

Noren, C.J. et al., *Science*, vol. 244, pp. 182–188 (1989).

Piccirilli et al., *Nature*, vol. 343, pp. 33–37 (Jan. 4, 1990).

Randerath et al., *Meth. in Enzymology*, vol. 65, pp. 638–680 (1980).

Sarver, N. et al., *Science*, vol. 247, pp. 1222–1225 (1990).

Sepiol et al., *Z. Naturforsch*, vol. 31e, pp. 361–370 (1976).

Sgaramella, V. et al., *J. Mol. Biol.*, vol. 72, pp. 427–444 (1972).

Switzer et al., *J. Am. Chem. Soc.*, vol. 111, pp. 8322–8323 (1989).

Switzer et al., *Biochem.*, vol. 32, pp. 10489–10496 (1993).

Szostak, J., *Nature*, vol. 322, pp. 83–86 (1986).

Voegel, J.J. et al., *J. Org. Chem.*, vol. 58, pp. 7542–7547 (1993).

Watanabe et al., *Nucleic Acid Chemistry*, eds. Tipson, Townsend, John Wiley & Sons, New York, pp. 273–277 (1978).

Zubay, G., *Roots of Modern Biochem.*, eds. Klein Kauf, von Dohren, Jeanicke, Walter de Gruyter & Co., Berlin, pp. 911–916 (1988).

* cited by examiner

METHODS FOR PREPARING OLIGONUCLEOTIDES CONTAINING NON-STANDARD NUCLEOTIDES

CROSS REFERENCE TO RELATED APPLICATIONS

This application is a Continuation of application Ser. No. 08/775,401, filed Dec. 31, 1996, now U.S. Pat. No. 6,140,496, which is a Continuation-in-Part of application Ser. No. 08/542,142, filed Oct. 12, 1995, now U.S. Pat. No. 6,037,120, and a Continuation-in-Part of application Ser. No. 08/375,132, filed Jan. 17, 1995, now U.S. Pat. No. 6,001,983, which is a Continuation-in-Part of application Ser. No. 07/594,290, filed Oct. 9, 1990, now U.S. Pat. No. 5,432,272, which application(s) are incorporated herein by reference.

Statement of rights to inventions made under Federally-sponsored research: None

INTRODUCTION

1. Field of the Invention

The field of this invention is nucleic acids and their analogs, more specifically nucleoside building blocks for preparing oligonucleotide analogs capable of forming non-standard Watson-Crick base pairs, joined by non-standard patterns of hydrogen bonding, those different from hydrogen bonding patterns joining the standard adenine-thymine and cytosine-guanine base pairs.

2. Background of the Invention

Natural oligonucleotides bind to complementary oligonucleotides according to the well-known rules of base pairing first elaborated by Watson and Crick, where adenine (A) pairs with thymine (T) or uracil (U), and guanine (G) pairs with cytosine (C), with the complementary stands anti-parallel to one another. These pairing rules allow for the specific hybridization of an oligonucleotide with complementary oligonucleotides, making oligonucleotides valuable as probes in the laboratory, in diagnostic applications, as messages that can direct the synthesis of specific proteins, and in a wide range of other applications well known in the art. Further, the pairing is the basis by which enzymes are able to catalyze the synthesis of new oligonucleotides that are complementary to template nucleotides. In this synthesis, building blocks (normally the triphosphates of ribo or deoxyribo derivatives of A, T, U, C, or G) are directed by a template oligonucleotide to form a complementary oligonucleotide with the correct sequence. This process is the basis for replication of all forms of life, and also serves as the basis for all technologies for enzymatic synthesis and amplification of specific heterosequence nucleic acids by enzymes such as DNA and RNA polymerase, and in the polymerase chain reaction.

The Watson-Crick pairing rules can be understood chemically in terms of the arrangement of hydrogen bonding groups on the heterocyclic bases of the oligonucleotide, groups that can either be hydrogen bond donors or acceptors (FIG. 1). In the standard Watson-Crick geometry, a large purine base pairs with a small pyrimidine base thus, the AT base pair is the same size as a GC base pair. This means that the rungs of the DNA ladder, formed from either AT or GC base pairs, all have the same length.

Further recognition between bases is determined by hydrogen bonds between the bases. Hydrogen bond donors are heteroatoms (nitrogen or oxygen in the natural bases) bearing a hydrogen; hydrogen bond acceptors are heteroatoms (nitrogen or oxygen in the natural bases) with a lone pair of electrons. In the geometry of the Watson-Crick base pair, a six membered ring (in natural oligonucleotides, a pyrimidine) is juxtaposed to a ring system composed of a fused six membered ring and a five membered ring (in natural oligonucleotides, a purine), with a middle hydrogen bond linking two ring atoms, and hydrogen bonds on either side joining functional groups appended to each of the rings, with donor groups paired with acceptor groups (FIG. 1).

Derivatized oligonucleotide building blocks, where a side chain has been appended to one of the nucleoside bases A, T, U, G, or C (the "normal" bases), have application because of their combination of Watson-Crick base pairing and special reactivity associated with the chemical properties of the side chain. For example, oligonucleotides containing a T to which is appended a side chain bearing a biotin residue can first bind to a complementary oligonucleotide, and the hybrid can then be isolated by virtue of the specific affinity of biotin to avidin (Langer, P. R.; Waldrop, A. A.; Ward, D. C. (1981) *Proc. Nat. Acad. Sci.* 78, 6633–6637), and finds application in diagnostic work. Oligonucleotides containing special functional groups (e.g., thiols or hydrazines) can be immobilized to solid supports more readily than those composed solely of the five "natural" bases. Additionally, radiolabeled nucleotide bases can be included in an oligonucleotide, for example, $^3H$ or $^{32}P$ labeled nucleotide bases.

Often, derivatized building blocks can be incorporated into oligonucleotides by enzymatic transcription of natural oligonucleotide templates in the presence of the triphosphate of the derivatized nucleoside, the substrate of the appropriate (DNA or RNA) polymerase. In this process, a natural nucleoside is placed in the template, and standard Watson-Crick base pairing is exploited to direct the incoming modified nucleoside opposite to it in the growing oligonucleotide chain.

However, the presently available base pairs are limited in that there are only two mutually exclusive hydrogen bonding patterns available in natural DNA. This means that should one wish to introduce a modified nucleoside based on one of the natural nucleosides into an oligonucleotide, it would be incorporated wherever the complementary natural nucleoside is found in the template. For many applications, this is undesirable.

Further, in many applications, it would be desirable to have base pairs that behave as predictably as the AT and GC base pairs, but that do not pair with natural oligonucleotides, which are built from A, T, G, and C.

Many of the limitations that arise from the existence of only four natural nucleoside bases, joined in only two types of base pairs via only two types of hydrogen bonding schemes, could be overcome were additional bases available that could be incorporated into oligonucleotides, where the additional bases presented patterns of hydrogen bond donating and accepting groups in a pattern different from those presented by the natural bases, and therefore could form base pairs exclusively with additional complementary bases. The purpose of this invention is to provide compositions of matter containing these additional bases, and methods for using them to recognize complementary oligonucleotide strands also containing non-standard bases. A "non-standard" nucleobase is one that presents to a nucleobase on a complementary strand, placed in a Watson-Crick geometry, a pattern of hydrogen bond donor and acceptor groups different from those found in adenine or 2-aminoadenine, guanine, cytosine, and thymine or uracil.

SUMMARY OF THE INVENTION

The compositions of this invention are precursors and building blocks for deoxyribonucleic acid (DNA) and ribo-nucleic acid (RNA) containing non-standard nucleobases, including ribo and deoxynucleosides bearing non-standard nucleobases, ribo and deoxynucleosides having protected exocyclic amino group functionality, protected and activated ribo and deoxynucleosides suitable for solid phase DNA and RNA synthesis, and ribo and deoxynucleoside phosphates suitable for enzymatic synthesis of DNA and RNA.

DETAILED DESCRIPTION OF THE INVENTION

The objective of this invention is to provide an expanded molecular recognition system based on an increased number of independently recognizable building blocks that can be incorporated into DNA and RNA. The objective is accomplished by incorporating into double stranded DNA and RNA base pairs composed of pairing units that fit the Watson-Crick geometry in that they involve a monocyclic six membered ring pairing with a fused bicyclic heterocyclic ring system composed of a five member ring fused with a six membered ring, with the orientation of the heterocycles with respect to each other and with respect to the backbone chain analogous to that found in DNA and RNA, but with a "non-standard" pattern of hydrogen bonds holding the base pair together different from that found in the AT and GC base pairs (the "standard" base pairs). The invention also provides a process which includes incubating an oligonucleotide template containing one or more non-standard bases with either a DNA or RNA polymerase in the presence of triphosphates of the complementary nucleotides.

This invention is based on the fact that novel bases with patterns of hydrogen bond donors and acceptors that are different from those found in the normal A-T (or A-U) and G-C base pairs can fit the standard Watson-Crick geometry. Thus, in the naturally-occurring Watson-Crick base pairs, the pyrimidine components present an acceptor-donor-acceptor (T) or a donor-acceptor-acceptor (C) pattern of hydrogen bonds to a purine on an opposite strand. However, other patterns are possible. For example, FIG. 2 discloses four base pairs that have still different patterns, an acceptor-acceptor-donor pattern for iso-C (pyAAD), and donor-acceptor-donor pattern for K (pyDAD). Bases, pairing schemes, and base pairs that have hydrogen bonding patterns different from those found in the AT and GC base pairs are here termed "non-standard". Although not found (to our knowledge) in natural encoding nucleic acids, the non-standard base pairs shown in FIG. 2 can fit into the DNA ladder in a standard Watson-Crick duplex.

Figure 1:
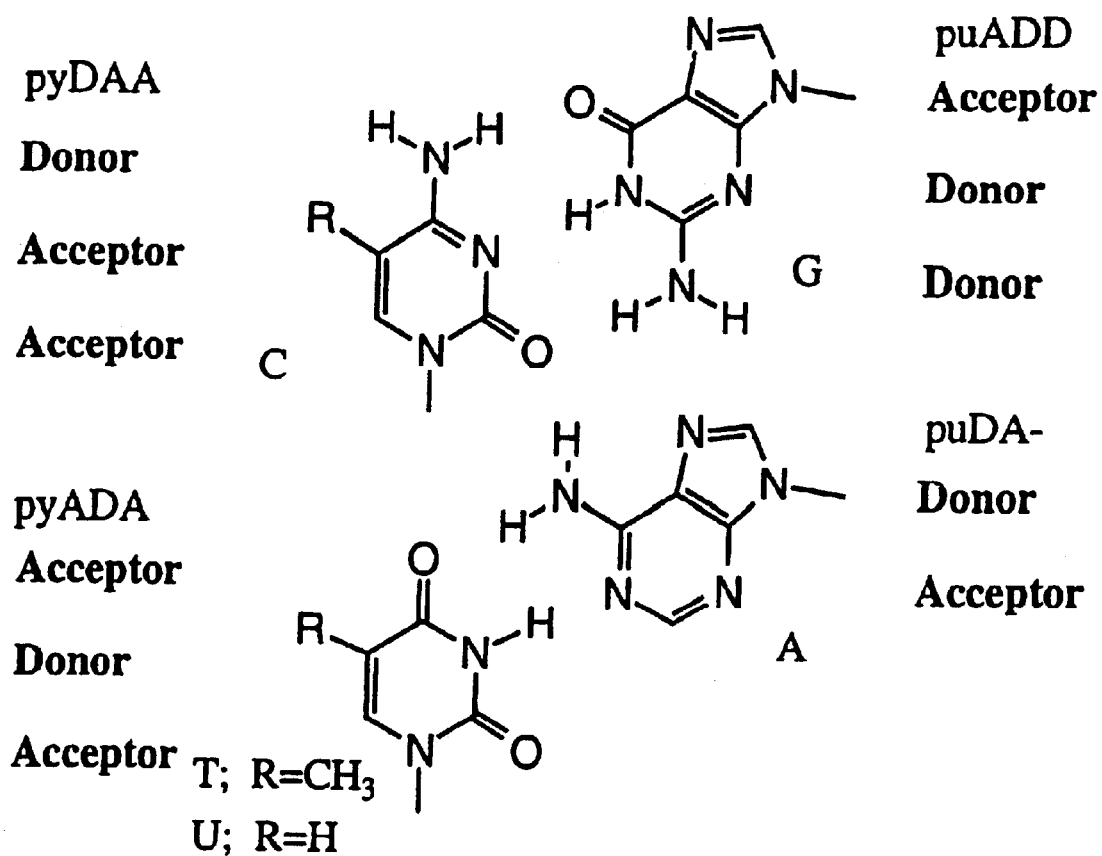
FIG. 1 shows the two standard base pairs formed between the standard bases, e.g. C and G; T and A. To systematize the nomenclature for standard nucleobases, pyrimidines are designated by the prefix "py", purines by the prefix "pu". Following the prefix is the order, from the major groove to the minor groove, of acceptor (A) and donor (D) groups. Thus, both thymine and uracil implement the standard hydrogen bonding pattern pyADA. The standard nucleobase cytosine implements the standard hydrogen bonding pattern pyDAA. The standard nucleobases adenine and guanine implement the standard hydrogen bonding pattern puDA- and puADD respectively.
Figure 2:
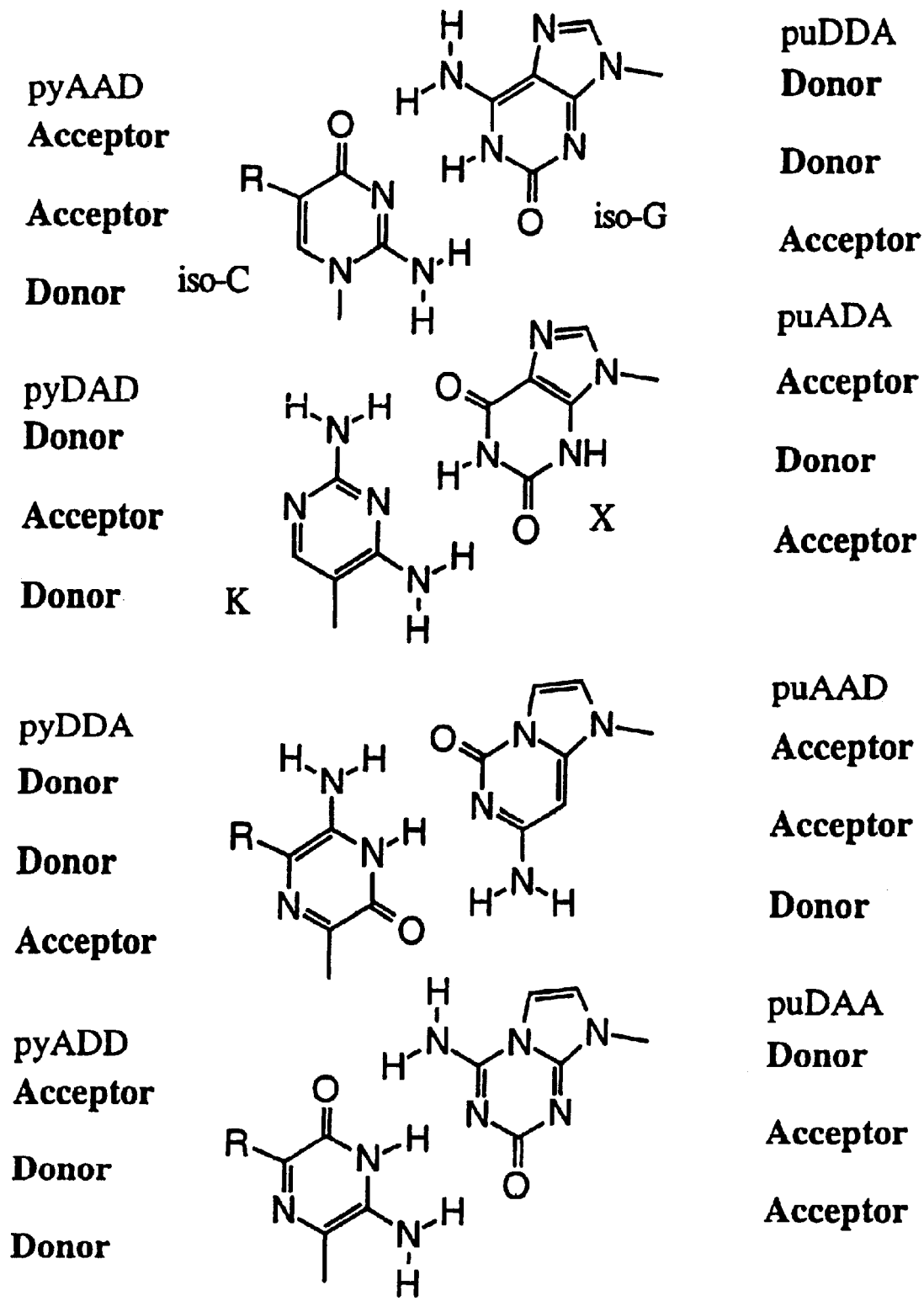
FIG. 2 shows the specific structures of eight different base pairs that include the preferred embodiments according to the subject invention. To systematize the nomenclature for non-standard nucleobases, pyrimidines are designated by the prefix "py", purines by the prefix "pu". Following the prefix is the order, from the major groove to the minor groove, of acceptor (A) and donor (D) groups.
Figure 3:
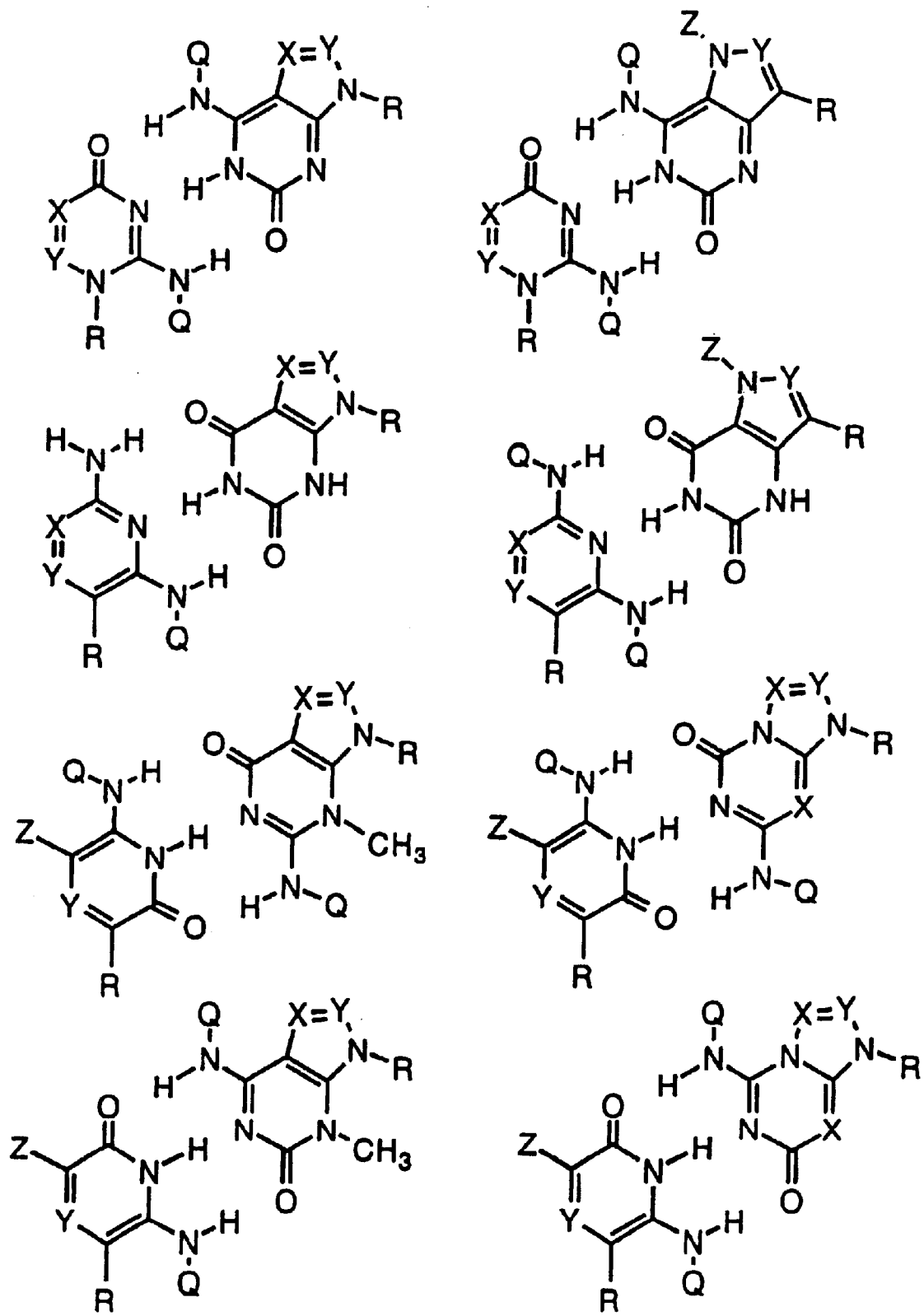
FIG. 3 shows the general structures of eight different base pairs according to the subject invention. The notation -R designates the point of attachment of the ribose, deoxyribose, or ribose or deoxyribose derivative, X is either a nitrogen atom or a carbon atom bearing a substituent Z, Z is either a, hydrogen, an unfunctionalized lower alkyl, alkynyl, or alkyl-alkynyl chain, or a lower alkyl, alkynyl, or alkyl-alkynyl chain bearing an amino, trifluoroacetamido, carboxyl, hydroxy, thiol, aryl, indole, or imidazoyl group, Y is either N or CH, and Q is selected from a group consisting of hydrogen, benzoyl, p-tertbutylbenzoyl, dialkylformamidyl, and p-nitrophenylethyl, and the ring contains no more than three nitrogens consecutively bonded.

Further, the patterns of hydrogen bonds in these non-standard pyrimidines are different from each other, and different from those in the natural pyrimidines T and C. This suggested that in an enzyme-catalyzed polymerization, it might be possible for each non-standard pyrimidine to recognize uniquely its complementary purine with high fidelity. Thus, it should be possible to make DNA strands containing all 12 bases that recognize complementary DNA strands following an expanded set of Watson-Crick rules: A pairs with T, G pairs with C, pyAAD pairs with puDDA and pyDAD pairs with puADA, pyDDA pairs with puAAD, and pyADD pairs with puDAA (FIG. 2). In other words, it should be possible to have a oligonucleotide-like molecular recognition system with twelve bases instead of four.

Statements considering non-standard base pairs in a general way can, to our knowledge, be found only four times previously in the literature. Considering possible bases that might have been incorporated into nucleic acids in the first forms of life on the earth two to four billion years ago, Rich mentions the base pair between iso-C and iso-G (Rich, A. (1962), *Horizons in Biochemistry*. Kasha, M. and Pullman, B. editors, N.Y., Academic Press, 103–126) as a base pair that was conceivable, but rejected, by the earliest forms of life. However, Rich did not disclose nor make obvious the method disclosed here where oligonucleotide strands containing non-standard bases would recognize complementary oligonucleotides incorporating the base pair between iso-C and iso-G into oligonucleotides. Indeed, shortly before, Dekker suggested in a review article that the iso-C nucleoside is chemically unstable (Dekker, C. (1960) *Ann. Rev. Biochem.* 464). Saenger (Saenger, W. (1985) *Nucleic Acid Chemistry*, Springer-Verlag) also mentions this base pair, but concludes, based on the fact that iso-G has alternate tautomeric forms (vide infra), that it has no utility as part of an oligonucleotide that is to be copied.

Zubay (Zubay, G. (1988) *The Roots of Modern Biochemistry*, Kleinkauf, von Doehren, Jaenicke, Berlin, Walter de Gruyter & Co. 911–916) suggested that 2,4-diamino-5,6-dihydropyrimidine-1-riboside, with a donor-acceptor-donor pattern, might be able to pair with xanthosine. In Zubay's suggested pyrimidine, however, the pyrimidine ring is not aromatic and therefore not planar. Although it has never been examined experimentally, we believe on these grounds that it would not participate well in "base stacking," the interaction (vide supra) that is important for the stability of a double helix. Further, Zubay's base incorporates the structural unit known as a "vinylogous enamine", a structural unit that is likely to be unstable in acidic solution. Thus, we doubt that it can be incorporated into an oligonucleotide by enzymatic transcription of a complementary oligonucleotide.

Zubay discloses neither experimental studies with his suggested base nor the potential utility of a new base pair that would arise were the new base a substrate for DNA and RNA polymerases present in the modem world. Further, the possibility of constructing additional base pairing schemes (such as the non-standard base pairs disclosed in FIG. 2) was explicitly denied. Zubay writes "We have searched for other purine-pyrimidine base pairs with different arrangements of hydrogen bonding groups that would satisfy the criterion of exclusive pairing. No additional pairs have been found. Thus except for modifications at non-hydrogen bonding sites the additional base pair described here may be unique." This comment from a prominent figure in American biochemistry supports the notion that the invention disclosed here, where non-standard base pairs in oligonucleotides expand the molecular recognition properties of these molecules, is not obvious to one skilled in the art.

Additional literature has discussed nucleosides that could perform as a component of a non-standard base pair, but evidently without the realization that non-standard base pair is possible. For example, iso-G is a component of the natural product crotonoside, which is a ribonucleoside analog. The chemistry of the iso-G riboside was studied in the 1970's by Shugar and his coworkers (Golar, T., Fikus, M., Kazimierczuk, Shugar, D. (1976) Eur. J. Biochem. 65, 183–192; Sepiol, J., Kazimierczuk, Z., Shugar, D. (1976) Naturforsch. 31c, 361). Chu et al. reported the synthesis of a pyrimidine donor-acceptor-donor non-standard nucleoside (Chu, C. K., Reichman, U., Watanabe, K. A., & Fox, J. J. (1977) J. Org. Chem. 42, 711–714), but again without reference to potential Watson-Crick base pairing. Further, we are unaware of the preparation of deoxynucleoside derivatives bearing these non-standard nucleobases. Oligodeoxyribonucleotides, because of the absence of 2'-hydroxyl groups, are more stable to hydrolytic cleavage than the corresponding oligoribonucleotides. Similar stability can be achieved with 2'-O-methoxyribonucleotides, as is well known in the art.

Should the additional base pairs disclosed in FIG. 2 be placed into DNA and RNA, they could be useful for a variety of purposes. For example, RNA molecules prepared by transcription, although it is known to be a catalyst under special circumstances ((a) Cech, T. R.; Bass, B. L (1986). Ann. Rev. Biochem. 55, 599. (b) Szostak, J. W. (1986) Nature 332, 83. (c) Been, M. D.; Cech, T. R. Science 1988, 239, 1412), appear to have a much smaller catalytic potential than proteins because they lack building blocks bearing functional groups. Conversely, the limited functionality present on natural oligonucleotides constrains the chemist attempting to design catalytically active RNA molecules, in particular, RNA molecules that catalyze the template-directed polymerization of RNA.

Additional base pairs could relax these constraints, especially if their hydrogen bonding pattern differed from those in the AT and GC base pairs, as novel hydrogen bonding schemes would allow additional base pairs to be incorporated enzymatically at specific positions in an oligonucleotide molecule (Switzer, C. Y, Moroney, S. E., Benner, S. A. (1989) J. Am. Chem. Soc. 111, 8322). If functionalized, such additional bases should also allow the incorporation of functional groups directly into RNA; the remaining unfunctionalized building blocks could then control secondary structure without introducing over-functionalization and attendant non-specific catalysis. Further, bases bearing functional groups at the position structurally analogous to the 5-position of the uridine ring should be substrates for most polymerases (Leary, J. L., Brigati, D. J., Ward, D. C. (1983) Proc. Natl. Acad. Sci. 80, 4045). New base pairs should also find use in studies of the structure of biologically important RNA and DNA molecules (Chen, T. R., Churchill, M. E. A. Tullius, T. D. Kallenbach, N. R., Seemann, N. C. (1988) Biochem. 27, 6032) and protein-nucleic acid interactions. Several types of catalytic RNA molecules containing natural bases have been proposed as anti-viral agents, for use in agriculture, and in other areas (Haseloff, J., Gerlach, W. L. (1988) Nature 334, 585; Sarver, N., Cantin, E. M., Chang, P. S., Zaia, J. A., Ladne, P. A., Stephens, D. A., Rossi, J. J. (199) Science 247, 1222–1225). Catalytic RNA molecules incorporating additional bases should be even more useful in certain of these applications. A segment of DNA or RNA containing the non-standard bases could be recognized only by complementary oligonucleotides containing the complementary non-standard bases, allowing the selective copying of DNA containing the additional bases in the presence of DNA containing normal bases, and vice versa More speculatively, the extra letters in the nucleoside alphabet might eventually be used to expand the genetic code, increasing the number of amino acids that can be incorporated translationally into proteins (Noren, C. J., Anthony-Cahill, S. J., Griffith, M. C. & Schultz, P. G. (1989) Science 244, 182; J. D. Bain, J C. G. Glabe, T. A. Dix, A. R. Chamberlain (1989) J. Am. Chem. Soc. 111, 8013–8014). Additionally, radiolabeled non-standard nucleotide bases can be included in an oligonucleotide.

Finally, and most generally, non-standard bases incorporated into oligonucleotides might provide a molecular recognition system that has the "rule-based" behavior of DNA and RNA, but which does not bind to complementary DNA and RNA from natural systems. Such a molecular recognition system should have use in building nanostructures, in diagnostics, and in forensic medicine.

The preferred non-standard base pairs for expanding the diversity of the molecular recognition properties of oligonucleotides are formed between pyAAD and puDDA, and between 3-β-D-ribofuranosyl-(2,6-diaminopyridine), designated here as either pyDAD or K, and several complementary purines, in particular, xanthosine and 3-β-D-ribofuranosyl-(1-methylpyrazolo[4,3-d]pyrimidine-5,7(4H, 6H)-dione), all of which implement the non-standard puADA hydrogen bonding pattern. To maximize stability of the oligonucleotide containing the non-standard nucleobase, a backbone composed of 2'-deoxyribosides or 2'-O-methoxyribosides is preferred. To permit ready incorporation of nucleotides bearing non-standard nucleobases via automated chemical synthesis of oligonucleotides, the 5'-dimethoxytrityl protecting group is preferred on the 5'-oxygen of the ribose derivative, with the 3'-oxygen bearing a phosphoramidite derivative suitable for coupling in oligonucleotide synthesis procedures well known in the art. While many combinations of heterocycles and protecting groups are adequate, the presently preferred embodiment of the instant invention uses the following combinations:

pyDAD. The presently preferred embodiment is a diaminoyprimidine heterocycle with the exocyclic amino groups protected as p-tertbutylbenzoyl amides.

puADA. The presently preferred embodiment is a xanthine heterocycle with the exocyclic oxygens protected as p-notophenylethyl ethers.

pyAAD. The presently preferred embodiment is a 5-methyl-isocytosine heterocycle with the exocyclic amino group protected as its N,N-dibutylformamidine.

puDDA. The presently preferred embodiment is an isoguanine heterocycle with the exocyclic amino group protected as its N,N-dibutylformarmidine.

pyDDA. The presently preferred embodiment is a 2-amino-3-methyl-6-hydroxy pyrazine heterocycle with the exocyclic amino group protected as its N,N-dibutylformarmidine.

puAAD. The presently preferred embodiment is a 5-aza-3,7-dideazaguanosine heterocycle with the exocyclic amino group protected as N,N-dibutylformamidine.

pyADD. The presently preferred embodiment is a 6-amino-3-methyl-2-hydroxy pyrazine heterocycle with the exocyclic amino group protected as its N,N-dibutylformamidine.

puDAA. The presently preferred embodiment is a 4-amino-1,3,5-triazin-2(8H)-one heterocycle with the exocyclic amino group protected as its N,N-dibutylformamidine.

To permit ready incorporation of nucleotides bearing non-standard nucleobases via enzymatic synthesis of oligonucleotides, the 5'-triphosphate derivatives are preferred. Corresponding nucleoside 5'-diphosphates, 5'-monophosphates, and 3'-monophosphates bearing non-standard nucleobases are useful as analytical standards and synthetic intermediates, as well understood by those of ordinary skill in the art.

Both the pyADD and pyDDA ribosides undergo a slow epimerization that interconverts the beta and alpha anomers (von Krosigk, U., Benner, S. A. *J. Am. Chem. Soc.* 117, 5361–5362 (1995); Vögel, J. J., von Krosigk, U., Benner, S. A. Synthesis and tautomeric equilibrium of 6-amino-5-benzyl-3-methylpyrazin-2-one. An acceptor-donor-donor nucleoside base analog. *J. Org. Chem.* 58, 7542–7547 (1993)). Therefore, for many applications, including triple helix formation, either a carbocyclic analog where the furanose ring oxygen is replaced by a $CH_2$ group, or a ribose derivative where a lower alkyl, most preferably methyl, group is atached to the 2'-oxygen, is preferred. 2'-O-alkyl derivatives are also useful for the other non-standard ribonucleosides as components of oligonucleotides, as will be appreciated to one of ordinary skill in the art.

Phosphate derivatives of the non-standard nucleosides are useful as synthetic intermediates and as analytical standards. The corresponding thiophosphates are also useful, as will be appreciated by one of ordinary skill in the art.

Last, 2',3'-dideoxynucleoside derivatives bearing non-standard nucleobases have value in sequencing protocols, as will be appreciated by one of ordinary skill in the art.

EXPERIMENTAL

EXAMPLE 1

Ribose Derivatives of iso-cytosine

The general procedures can be found in Switzer, C. Y., Moroney, S. E., Benner, S. A. (1993) *Biochemistry* 32, 10489–10496), which areincorporated herein by reference, as are other citations throughout this disclosure.

iso-Cytidine. Ribo-iso-cytidine was prepared by the method of Kimura et al. (Kimura, J., Yagi, K., Suzuki, H., & Mitsunobu, O. (1980) *Bull. Soc. Chem. Jap.* 53, 3670–3677).

iso-Cytidine triphosphate. Tris-(tributylammonium) pyrophosphate was prepared by treating pyrophosphoric acid (293 mg) in water (2.0 mL) with tributylamine (1.2 mL). The mixture was stirred vigorously at 0° C. for 10 min, and then at room temperature (RT) for 1 h. The water was removed by lyophilization: the residue was further dried by coevaporation with pyridine (3×5 mL) and toluene (5 mL), and then by evacuation (0.25 mm pressure, 12 h). The tris-(tributylammonium) pyrophosphate residue was dissolved in dimethylformamide (2.5 mL) and the solution used for subsequent reactions.

Separately, iso-cytidine (80 mg, 0.33 mM) was suspended in trimethylphosphate (0.822 mL, 7.0 mM) at 0° C. The suspension was treated with $POCl_3$ (0.039 mL, 0.4 mM), and the mixture stirred for 1.5 h. The solution of tris-(tri-n-butylammonium) pyrophosphate in dimethylformamide from above was rapidly added and the mixture agitated vigorously for 1 min. A solution of $Et_3NH^+$ bicarbonate (1 M, pH 8.0, 2.0 mL) was then added. TLC ($SiO_2$, propanol:ammonia:water 11:7:2) and HPLC (100 mM $Et_3NH^+$ acetate pH 7.0 (A), acetonitrile (B), 100% A to 80% A/20% B over 30 min) showed a mixture of iso-C, iso-CMP, and iso-CTP. The mixture was resolved by chromatography on Sephadex A-25 (formate form, 30 mL) eluted with a gradient of $Et_3NH^+$ formate (0.2 to 1.5 M). The iso-CTP eluted last (overall yield, 21%), was recovered by lyophiilization, and shown to be free of iso-C and iso-CMP by HPLC. $^{31}$P-NMR: −10.175, −11.0, −21.725, in water; FAB-MS (M−H)$^-$ 482.2).

EXAMPLE 2

2'-Deoxyribose Derivatives of iso-cytosine 2,5'-Anhydro-2'-deoxyuridine. 2,5'-Anhydro-2'-deoxyuridine was prepared by the method of Watanabe et al. (Watanabe, K. A., Reichman, U., Chu, C. K., & Fox, J. J. (1978) *Nucleic Acid Chemistry*, Tipson, R. S., & Townsend, L. B., Eds.) Part 1, pp 273–277, Wiley, N.Y.).

2'-Deoxy-iso-cytidine. Unprotected 2'-deoxy-iso-cytidine was prepared by a procedure adapted from the literature for the preparation of the ribose derivative (Kimura et al., 1980). Methanol (50 mL) was saturated with dry $NH_3$ at 0° C., and 2,5'-anhydro-2'-deoxyuridine (450.6 mg, 2.14 mmol) added as a solid. The mixture was stirred at RT for 3 days. TLC ($SiO_2$, 20% $MeOH/CH_2Cl_2$) showed essentially complete conversion. Stirring was continued for an additional 5 days, the solvents removed by evaporation, and d-iso-cytidine recovered in essentially quantitative yield. FAB-MS (M+1)$^+$ 228.1.

N-Benzoyl-2'-deoxy-iso-cytidine. A mixture of 2'-deoxy-iso-cytidine (53 mg, 0.25 mmol), benzoic anhydride (59 mg, 0.25 mmol) and pyridine (2.0 mL) was stirred under $N_2$ overnight. The mixture was then diluted with water and extracted with $CH_2Cl_2$. The organic extracts were dried ($MgSO_4$), evaporated, and the residue chromatographed ($SiO_2$, 8% $MeOH/CH_2Cl_2$) to yield N-benzoyl-2'-deoxy-iso-cytidine (32.7 mg, 40%, FAB MS (M+H)$^+$ 332.0805).

N-Benzoyl-2'-deoxy-5'-dimethoxytrityl-iso-cytidine. N-Benzoyl-d-iso-cytidine (48 mg, 0.145 mmol) from the previous step was dried by coevaporation with pyridine (2×3 mL). To the residue was added dimethoxytrityl chloride (59 mg, 0.174 mmol) and dimethylaminopyridine (2 mg, 0.11 equiv.) as solids. Pyridine (1.5 mL, distilled from $CaH_2$) and triethylamine (0.028 mL, 0.203 mmol, distilled from $CaH_2$) were added. The mixture was stirred at RT for 2 h, diluted with water (15 mL) and extracted with ether. The organic extracts were dried ($MgSO_4$), evaporated, and the residue chromatographed ($SiO_2$, 8% $EtOAc/CH_2Cl_2$ 1:10) to yield N-benzoyl-2'-deoxy-5'-dimethoxytrityl-iso-cytidine (63 mg, 68%, FAB MS (M+H)$^+$=634.3) as a yellow foam.

$N^2$-Benzoyl-5'-dimethoxytrityl-d-iso-cytidine phosphoramidite. The phosphoramidite of protected 2'-deoxy-iso-cytidine was prepared following the procedure of Moore and Beaucage (1985). The tritylated base (31.7 mg, 0.05 mmol) was placed in a vial under $N_2$ (1 mL) together with 4,5- dichloroimidazole (24.5 mg, 0.179 mmol) and 1-methyl-2-pyrrolidinone (NMP, 0.3 mL). The solution was then transferred to another vial (1 mL) containing bis-(diisopropylamino)-methoxyphosphine (13.11 mg) under $N_2$. The first vial was washed with NMP (0.20 mL), and the washings added to the second vial. The mixture was stored at RT under $N_2$, and used in the synthesis of the appropriate oligodeoxynucleotides.

2'-Deoxy-iso-cytidine-3'-monophosphate. 1,2,4-Triazole (207 mg, dried under high vacuum overnight) in dioxane (10 mL, distilled from Na/benzophenone) was treated under $N_2$ at RT with $POCl_3$ (0.092 mL) and then triethylamine (0.418 mL, distilled from $CaH_2$) over a period of 15 min. The mixture was stirred under $N_2$ at RT for 40 min and then filtered under $N_2$ to yield a solution of tris-(triazolo)-phosphine oxide (0.1 M). N-Benzoyl-2'-deoxy-5'-dimethoxytrityl-iso-cytidine (63.4 mg, 0.010 mmol) was dissolved in pyridine (0.40 mL), and treated with the solution of tris-(triazolo)-phosphine oxide (0.02 mmol). The mixture was stirred at RT for 3 h. diluted with water (0.4 mL), and stirred at RT overnight. $NH_4OH$ (25%, 2.0 mL) was then added with pyridine (0.20 mL), the mixture heated at 60° C. for 12 h, kept at −20° C. overnight, and concentrated by evaporation under reduced pressure. The residue was treated with AcOH (80%, 1.0 mL) for 20 min, concentrated first by evaporation under reduced pressure, and then with absolute EtOH. The residue was dissolved in water (1.0 mL) and extracted with ether (3×1.0 mL). TLC (2-propanol:water:$NH_4OH$ 11:2:7) showed a single predominant spot corresponding to 2'-deoxy-iso-cytidine-3'-monophosphate (42% yield).

2'-Deoxy-iso-cytidine triphosphate. A suspension of 2'-deoxy-iso-cytidine (75 mg, 0.33 mmol) in trimethylphosphate (0.822 mL) at 0° C. was treated with $POCl_3$ (0.039 mL) and stirred for 1.5 h. To this mixture was then rapidly added a solution of tris-(tri-n-butylammonium) pyrophosphate (1.2 g) in dimethylformamide (2.5 mL) prepared as described above. The mixture was agitated vigorously for 1 min. A solution of $Et_3NH^+$ bicarbonate (1 M, pH 8.0, 2.0 mL) was then added, and the solvents removed by evaporation. The residue was dissolved in water (10 mL) and the mixture resolved by chromatography on Sepahadex A-25 (formate form. 30 mL) eluted with a gradient of $Et_3NH^+$ formate (0.2 to 1.5 M, pH 6.8). Further purification could be achieved by HPLC (TSK ODS-3 column, eluted with $Et_3NH^+$ acetate over 20 minutes in a gradient of 0 to 40% $CH_3CN$). FAB-MS $(M+3)^-$ 466.0. The $^1H$ NMR spectrum showed no contaminating d-UTP. The triphosphate of d-iso-cytidine is unstable. After 6 weeks storage at −20° C., an aqueous solution of d-iso-CTP contains only ca. 35% of the original material. Therefore, d-iso-CTP was used immediately after preparation, and proton n.m.r. showed no detectable impurities in the samples used in work reported here. FAB-MS $(M+3)^-$ 466.0.

EXAMPLE 3

Ribose Derivatives of iso-guanosine iso-Guanosine Triphosphate. The procedure below was adapted from Mantsch et al. (Mantsch, H. H., Goia, I., Kezdi, M., Bârzu, O., Dânsoreanu, M., Jebeleanu, G., & Ty, N. G. (1975) *Biochemistry* 14, 5593–5601) and Kazimierczuk and Shugar (Kazimierczuk, Z., & Shugar, D. (1973) *Acta Biochim. Pol.* 20, 395–402). Hydrogen peroxide (30%, 3.5 mL) was added to a solution of $Na_2CO_3$ (2.6 g, 25 mmol) in water (25 mL). Maleic anhydride (2.45 g, 25 mmol) was then added, and the mixture stirred at 0° C. for 30 min, at which point all of the maleic acid had dissolved. Concentrated $H_2SO_4$ (1.5 mL) in water (7.0 mL) was then added at 0° C. The mixture was extracted with ether (8×25 mL), and the combined extracts stored at 0° C.

A solution of monopermaleic acid in water was obtained by evaporating 17.1 mL of the ether extracts in the presence, of water (2.0 mL) in a stream of air. The pH of the solution was adjusted to 7.0 with NaOH (1 M), and a solution of the disodium salt of ATP (276 mg, 0.5 mmol, Fluka. in 1 mL water, pH 7.0) added. The reaction mixture was stirred for 24 hours at RT and the pH adjusted to 4.5 with HCl (1 M). EtOH (absolute, 30 mL) was added, and the resulting precipitate recovered by centrifiugation, dissolved in water (2.0 mL), the pH adjusted to 4.5, and the product reprecipitated with ether. Chromatography (Dowex-1, bicarbonate form, eluted with a gradient of 0.01 to 1.0 M $NH_4HCO_3$ in water) yielded the N-oxide of ATP (208 mg, 73%).

The N-oxide (50 mg, 0.090 mmol) was dissolved in water (45 mL) and the solution placed in a quartz tube. This was immersed in a second quartz tube containing aqueous acetic acid (10%). The distance between the walls of the tubes was 0.5 cm. The mixture was irradiated for 2 h (loss of absorbance at 235 nm, temperature ca. 45° C.), the pH adjusted to 10 (25% $NH_4OH$) and the mixture stirred at RT overnight. Water was then removed under reduced pressure at 30° C., and the material purified by HPLC (TSK ODS 120-T semipreparative column), eluted as described above (retention time 14.14 min). Fractions containing product were lyophilized three times with water to remove buffer, to yield iso-guanosine triphosphate (8.18 mg, 12%) determined by UV spectroscopy ($\lambda_{max}$ 291 nm).

iso-Guanosine 5'-monophosphate was prepared by essentially the same procedure as above except that the N-oxide was submitted to photolysis directly after precipitation from ethano/water. The final product was purified by HPLC as before (3% yield).

EXAMPLE 4

Deoxyribose Derivatives of iso-guanosine

2'-Deoxy-iso-guanosine 3'-monophosphate was prepared by the same procedure used for the preparation of iso-guanosine 5'-triphosphate except that the N-oxide was submitted to photolysis directly after precipitation from ethanol/water. The final product was purified by HPLC and the amount of product determined spectrophotometrically (292 nm, e=11,000, 0.0208 mmol, 18% for two steps).

2'-Deoxy-iso-guanosine 5'-triphosphate was prepared by the same procedure used for the preparation of iso-guanosine 5'-triphosphate, except that the N-oxide was submitted to photolysis directly after precipitation from ethanol/water. The final product was purified by HPLC. The product (1.81 mmol, 2.6%) was determined by UV spectroscopy ($\lambda_{max}$=292 nm, e=11,000) (FAB-MS 504.6). $^{31}P$-NMR indicated that the product was free of impurities containing phosphorus. However, a small amount (ca. 10%) of an unidentified unphosphorylated impurity remained. This could not be removed either by HPLC or extended irradiation. No similar impurity was observed in either the preparation of iso-GTP or 2'-deoxy-iso-guanosine.

3',5'-O-Bis-tert.-butyldimethylsilyl-2'-deoxyadenosine N-oxide. To a solution of 3',5'-O-bis-tert.-butyldimethylsilyl-2'-deoxyadenosine (Ogilvie, K. K. (1973) *Can. J. Chem.* 51, 3799–3807.) (6.0 g, 12.5 mmol) in a mixture of EtOH and $H_2O$ (2.5:1) was added at RT monopermaleic acid (24 mmol). After 2 days, another 6 equiv. of monopermaleic acid were added, and the reaction continued for two weeks. Continuous monitoring (TLC on SiO$_2$, 10% MeOH in CH$_2$Cl$_2$) showed that the reaction did not proceed to completion even though peracid was still detectable (KI test). After two weeks, CH$_2$Cl$_2$ was added, the organic phase extracted with saturated NaHCO$_3$, and 3',5'-O-bis-tert.-butyldimethylsilyl-2'-deoxyadenosine N-oxide (3.41 g, 55%) isolated by chromatography (SiO$_2$, EtOAc:hexane 4:1) together with starting material (2.33 g, 39%).

3',5'-O-Bis-tert.-butyldimethylsilyl-2'-deoxy-iso-guanosine. N-oxide from the previous step (546 mg, 1.1 mmol) was dissolved in a mixture of EtOH (170 mL) and H$_2$O (170 mL). The solution was placed in a quartz reaction vessel with a mechanical stirrer, and irradiated with a mercury lamp for 6 hours. After irradiation, the pH of the mixture was adjusted to 10.0 (dilute NH$_4$OH), and the mixture stirred at RT overnight. In the morning, the pH was adjusted to 7.0 (10% HCl), the EtOH evaporated, the aqueous phase extracted with CH$_2$Cl$_2$, dried (MgSO$_4$), and 3',5'-O-bis-tert.-butyldimethylsilyl-2'-deoxy-iso-guanosine (330.9 mg, 60%) isolated by chromatography (SiO$_2$, eluted first with EtOAc until all of the 3',5'-O-bis-tert.-butyldimethylsilyl-2-deoxyadenosine eluted, and then with 20% MeOH in CH$_2$Cl$_2$).

N$^6$-(N,N-Dibutylformamidyl)-3',5'-O-di-tert.-butyldimethylsilyl-2'-deoxy-iso-guanosine. The general procedure was adapted from McBride et al. (1986). 3',5'-O-Bis-tert.-butyldimethylsilyl-2'-deoxy-iso-guanosine (292 mg, 0.59 mmol), N,N-dibutylformamidine dimethylacetal (0.405 mL, 1.77 mmol)(Frohler, B., Matteucci, M. (1983) *Nucleic Acids Research* 11, 8031) and pyridine (2.5 mL) were mixed and stirred at RT for 24 h. Complete conversion to a single product was indicated by thin layer chromatography (5% MeOH in CH$_2$Cl$_2$). Solvents were removed by evaporation, and the residue chromatographed (SiO$_2$, eluted with 5% MeOH in EtOAc) to yield the protected derivative of 2' deoxy-iso-guanosine (270 mg, 73%). UV $\lambda_{max}$=350 nm, 263 nm.

Removal of formamidine from d-iso-guanosine. Formamidyl-d-iso-guanosine (25 mg) was suspended in aqueous ammonia (25%, 1 mL) and ethanol (1 mL) and stirred at RT for 24 hours. Solvents were then evaporated, and the residue purified by HPLC (TSK OD5-3 column, eluted with aqueous Et$_3$NH$^+$ acetate in a gradient of 0 to 40% CH$_3$CN over 20 minutes). The half life for deprotection at 25° C. was 8 min. FAB-MS (M+H)$^+$ 268.1.

N$^6$-(N,N-Dibutylformamidyl)-O$^2$-(2-p-nitrophenethyl)-3',5'-O-di-tert.-butyldimethylsilyl-2'-deoxy-iso-guanosine. The general procedure was adapted from Himmelsbach et al. (1984). A mixture of formamidylated bis-TBDMS-d-iso-G (150 mg, 0.24 mmol), p-nitrophenethyliodide (133 mg, 0.48 mmol, prepared by treating 2-p-nitrophenylethanol with triphenylphosphite methiodide (Landauer, S. R., & Rydon, H. N. (1953) *J. Chem. Soc.* 2224.), Ag$_2$CO$_3$ (132 mg) and toluene (2.5 mL) was heated (80° C.) for 75 min. The mixture was then allowed to stand at RT for 1 h. Duplicate runs of the reaction were combined, filtered, and the protected product (243.8 mg, 65%) isolated by chromatography (SiO$_2$, hexane/EtOAc 65:35). FAB-MS (M+H)$^+$ 784.6.

N$^6$-(N,N-Dibutylformamidyl)-O$^2$-(2-p-nitrophenethyl)-2'-deoxy-iso-guanosine. The product of the previous step (219 mg, 0.28 mmol) in THF (0.19 mL) was treated with tetrabutylammonium fluoride on SiO$_2$ (43 mg, 0.84 mmol, Fluka). The reaction mixture was quenched via addition of NaHCO$_3$ (saturated solution), extracted with CH$_2$Cl$_2$, the extracts dried (MgSO$_4$), to yield N,N-dibutyl-N-formamidyl-O$^2$-(2-p-nitrophenethyl)-2'-deoxy-iso-guanosine (101.5 mg, 65%) isolated by chromatography (SiO$_2$, eluted with 10% MeOH in CH$_2$Cl$_2$). The low yield was caused by partial removal of the NPE group under these conditions.

N$^6$-(N,N-Dibutylformamidyl)-O$^2$-(2-p-nitrophenethyl)-2'-deoxy-5'-dimethoxytrityl-iso-guanosine. A mixture of the protected derivative of 2'-deoxy-iso-guanosine (93.3 mg, 0.168 mmol) from above, dimethoxytrityl chloride (68.3 mg, 0.202 mmol), and pyridine (2.0 mL) was stirred at RT for 2 h. MeOH (3 drops) was added, the solvents removed by evaporation, the residue taken up in CH$_2$Cl$_2$, and the organic layer washed with aqueous Na$_2$CO$_3$ (5%). The organic layer was concentrated, and N$^6$-(N,N-dibutylformamidyl)-O$^2$-(2-p-nitrophenethyl)-2'-deoxy-5'-dimethoxytrityl-iso-guanosine (105.3 mg, 73%) isolated by-chromatography (SiO$_2$, eluted with CH$_2$Cl$_2$:MeOH:pyridine 100:1:2).

Preparation of d-iso-guanosine phosphoramidite. Protected d-iso-guanosine (105.3 mg, 0.122 mmol), bis-(N,N-diisopropylamino)-3-cyanoethyloxyphosphine (Aldrich, 0.046 mL, 0.146 mmol, 1.2 equiv.), and diisopropylammonium tetrazolide (McBride, L. J., Kierzek, R., Beaucage, S. L. & Caruthers, M. H. (1986) *J. Am. Chem. Soc.* 108, 2040–2048)(10.4 mg, 0.06 mmol) were dissolved in CH$_3$CN (2.0 mL) and stirred for 1 h. The reaction was monitored by TLC (SiO$_2$ eluted with EtOAc:CH$_2$Cl$_2$:triethylamine 45:45:10). An additional portion (0.02 mL) of bis-(N,N-diisopropylamino)-3-cyanoethyloxyphosphine was then added, and stirring continued for an additional hour. Water (2 drops) was added, the mixture stirred for 15 min, the mixture diluted with CH$_2$Cl$_2$ (30 mL), and the organic layer washed with aqueous Na$_2$CO$_3$ (2%) and dried (Na$_2$SO$_4$). The phosphoramidite (120.3 mg, 93%) was isolated by chromatography (SiO$_2$, EtOAc:CH$_2$Cl$_2$:triethylamine 45:45:10 as eluant). $^{31}$P-NMR 149.74, 149.69.

EXAMPLE 5

Deoxyribose Derivatives of 2,4-Diaminopyrimidine

N$^2$,N$^4$-Di-(t-butyl-benzoyl)-2,4-diamino-5-(2',3'-isopropylidene-5'-O-trity-β-D-2'-ribofuranosyl)-pyrimidine. 2,4-Diamino-5-(2',3'-isopropylidene-5'-O-trityl-β-D-ribofuranosyl)-pyrimidine (9.4 g, 50 mmol) (Chu, C. K., Reichman, U., Watanabe, K. A., & Fox, J. J. (1977) *J. Org. Chem.* 42, 711–714) was treated with triethylamine (9.9 mL, 3 eq.), dimethylaminopyridine (300 mg), and trityl chloride (15.8 g, 1.1 equiv.). The mixture was stirred at RT for 24 h under argon. The reaction was quenched with water, and the aqueous and organic phases separated, and the organic solvents removed by rotary evaporation to yield 2,4-diamino-5-(2',3'-isopropylidene-5'-O-trityl-β-D-ribofuranosyl)-pyrimidine. This compound (2 g, 3.8 mmol) was evaporated three times with pyridine and dried at the high vacuum for 4–5 hours to remove any water. The oily, yellow residue was resolved in dry pyridine (40 mL) and cooled in an ice bath. At 0° C., t-butyl-benzoyl chloride (7.5 mL, 38 mmol, 5 eq.) were added dropwise over a period of (10 in) to the clear yellow solution. After a few minutes, a white compound started to precipitate and the suspension turned orange and later red. The progress of the reaction was monitored by tlc (hexane:EtOAc 3:1, product R$_f$=0.10)

After 2 hours at 0° C., the reaction was quenched by addition of water (4 mL), followed by ammonia-solution (30%, 5 mL) a few minutes later. The ice bath was removed and the yellow suspension was shaken 30–35 minutes at room temperature. The solvents were removed by rotary evaporation and the residue was dried at the high vacuum overnight to remove the pyridine.

The yellow residue was precipitated in ethyl acetate:hexane (1:3, 300 mL) and water (300 mL). The organic layers from the extraction were combined, dried over sodium sulfate, and filtered. The solvents were removed by rotary evaporated and dried at the high vacuum. The white-yellow residue was purified by column chromatography (silica gel, EtOAc:hexane 1:3) to give $N^2,N^4$-di-(t-butyl-benzoyl)-2,4-diamino-5-(2',3'-isopropylidene-5'-O-trityl-β-D-ribofuranosyl)-pyrimidine as a white-yellow foamy product (1.35 g; 42%).

$N^2,N^4$-Di-(t-butyl-benzoyl)-2,4-diamino-5-(β-D-ribofuranosyl)-pyrimidine. To a solution of $N^2,N^4$-di-(t-butyl-benzoyl)-2,4-diamino-5-(2',3'-isopropylidene-5'-O-trityl-β-D-ribofuranosyl)-pyrimidine (1.35 g; 1.58 mmol) in of dried methanol (10 mL), 10% (by weight) methanolic hydrogen chloride solution (2.5 mL) was added. After 90 min at room temperature, the tlc ($CHCl_3$:MeOH 11:2 ; product=$R_f$ 0.45) shows no more starting material. The reaction is stopped by bubbling argon gas through the solution for 30 min.

The clear orange solution was completely evaporated in vacuo and dried on the high vacuum overnight. The white-brown crude product was purified by column chromatography (silica, $CHCl_3$:MeOH 11:1) to yield $N^2,N^4$-di-(t-butyl-benzoyl)-2,4-diamino-5-β-D-ribofuranosyl)-pyrimidine (640 mg; 72%) as a white compound.

$N^2,N^4$-Di-(t-butyl-benzoyl)-2,4-diamino-5-(3',5'-O-[tetraisopropyldisiloxanyl]-β-D-ribofuranosyl)-pyrimidine. $N^2,N^4$-Di-(t-butyl-benzoyl)-2,4-diamino-5-(β-D-ribofuranosyl)-pyrimidine (932 mg; 1.66 mmol) was evaporated three times with pyridine and dried at the high vacuum overnight. The residue was resolved in 8.8 mL anhydrous pyridine and 0.58 mL tetraisopropyldisiloxane dichloride ($TPDSCl_2$) (1.82 mmol, 1.1 eq.) was added to the clear, yellow solution. The mixture was shaken at room temperature. During the reaction, a white compound starts to precipitate. The reaction was monitored by tlc (ethyl acetate:hexane 1:2; product $R_f$=0.25). After 4 hours, no starting material was detectable anymore. The reaction solution was evaporated and dried an the high vacuum overnight.

The residue was partitioned between chloroform (80 mL) and water (80 mL) and extracted with an additional chloroform (80 mL) and twice with brine (80 mL). The combined organic layers were dried over sodium sulfate and the solvents removed completely by rotary evaporation. The product was purified by chromatography (silica, EtOAc:hexane 1:2) to yield $N^2,N^4$-di-(t-butyl-benzoyl)-2,4-diamino-5-(3', 5'-O-[tetraisopropyldisiloxanyl]-β-D-ribofuranosyl)-pyrimidine (917 mg, 69%) as a white, foamy compound.

$N^2,N^4$-Di-(t-butyl-benzoyl)-2,4-diamino-5-(3',5'-O-[tetraisopropyidisiloxanyl]-2'-O[{imidazole-1-yl}thiocarbonyl]-β-D-ribofuranosyl)-pyrimidine. $N^2,N^4$-Di-(t-butyl-benzoyl)-2,4-diamino-5-(3',5'-O-[tetraisopropyl-disiloxanyl]-β-D-ribo-furanosyl)-pyrimidine (600 mg, 0.75 mmol) was dried at the high vacuum overnight, and then dissolved in DMF (7 mL). 1,1'-Thiocarbonyl-diimidazole (TCD) (306 mg, 1.72 mmol; 2 eq.) in DMF (3 mL) was added at room temperature. After 4 hours, the reaction was completed according to tlc (hexane:EtOAc 2:1, $R_f$=0.23). The mixture was quenched by addition of ethyl acetate (50 mL) and water (12 mL). The phases were separated, the organic layer was dried over sodium sulfate, and the filtrate was rotary evaporated. Overnight drying at the high vacuum yielded $N^2,N^4$-di-(t-butyl-benzoyl)-2,4-diamino-5-(3',5'-O-[tetraisopropyldisil- oxanyl]-2'-O-[{imidazole-1-yl}thiocarbanyl]-β-D-ribofuranosyl)-pyrimidine (740 mg, 108%). The crude material is used directly for the next step.

$N^2,N^4$-Di-(t-butyl-benzoyl)-2,4-diamino-5-(3',5'-O-[tetraisopropyldisiloxanyl]-2'-deoxy-β-D-ribofuranosyl)-pyrimidine. $N^2,N^4$-Di-(t-butyl-benzoyl)-2,4-diamino-5-(3', 5'-O-[tetraisopropyldisiloxanyl]2'-O[{imidazole-1-yl}thiocarbanyl]-β-D-ribofuranosyl)-pyrimidine (740 mg; 0.81 mmol), dried at the high vacuum overnight, was dissolved in anhydrous toluene (10 mL). Separately, 2,2'-azobisisobutyronitrile (AIBN) (97 mg, 0.59 mmol, 0.72 eq.) and tributyltin hydride (0.87 mL, 3.24 mmol, 4 eq.) were dissolved in toluene (5 mL). The two solutions were mixed and degassed with argon for one hour at room temperature. After turning off the gas, the solution was heated to 80° C. Gas generation was observed. By tlc (hexane:EtOAc 4:1, $R_f$=0.13), the reaction mixture showed no more starting material after 90 min. The solution was cooled to room temperature and the solvents completely removed by rotary evaporation. The product was isolated by chromatography on silica gel (hexane:EtOAc 4:1) to yield $N^2,N^4$-di-(t-butyl-benzoyl)-2,4-diamino-5-(3',5'-O-[tetraisopropyldisil-oxanyl]-2'-deoxy-β-D-ribofuranosyl)-pyrimidine (520 mg, 81%) as a white solid.

$N^2,N^4$-Di-(t-butyl-benzoyl)-2,4-diamino-5-(2'-deoxy-β-D-ribofuranosyl)-pyrimidine. $N^2,N^4$-Di-(t-butyl-benzoyl)-2,4-diamino-5-(3',5'-O-[tetraisopropyldisiloxanyl]2'-deoxy-β-D-ribofuranosyl-pyrimidine (690 mg; 0.87 mmol) were dissolved in anhydrous THF (4 mL). After addition of tetrabutyl ammonium fluoride (TBAF) (1.74 mL, 1.74 mmol), the clear and slightly yellow solution was shaken at ambient temperature for 45 min. The tlc ($CHCl_3$:MeOH 11:1) shows almost complete conversion to the product ($R_f$=0.22). The reaction mixture was evaporated completetly and the residue was directly purified by chromatography (silica, $CHCl_3$:MeOH 11:1) to yield $N^2,N^4$-di-(t-butyl-benzoyl)-2,4-diamino-5-(2'-deoxy-β-D-ribofuranosyl)-pyrimidine (423 mg, 89%).

$N^2,N^4$-Di-(t-butyl-benzoyl)-2,4-diamino-5-(5'-O-(4',4"-dimethoxytrityl)-2'-deoxy-β-D-ribofuranosyl)-pyrimidine. $N^2,N^4$-Di-(t-butyl-benzoyl)-2,4-diamino-5-(2'-deoxy-β-D-ribofuranosyl)-pyrimidine (423 mg, 0.77 mmol) were coevaporated with pyridine twice to remove all water. The foamy residue then was dissolved in pyridine (5 mL) and the clear, slightly yellow solution was combined with the dimethoxytrityl chloride (313 mg, 0.92 mmol), dissolved in another 5 mL of pyridine. The clear, yellow solution was shaken at room temperature for 4–5 hours. By then, the tlc ($CHCl_3$:MeOH 11:1) showed no further changes ($R_f$: product=0.60). The reaction was stopped by addition of water (0.3 mL). After evaporation of the mixture, the residue was partionated between EtOAc (40 mL) and saturated $NaHCO_3$ solution (40 mL). The combined organic layers were dried over sodium sulfate and filtered. The solvents were removed by rotary evaporation, and the residue chromatographed (silica, $CHCl_3$:MeOH 20:1) to yield $N^2,N^4$-di-(t-butyl-benzoyl)-2,4-diamino-5-(5'-O-(4',4"-dimethoxytrityl)-2'-deoxy-β-D-ribofuranosyl)-pyrimidine (495 mg, 76%) as a white foam.

$N^2,N^4$-Di-(t-butyl-benzoyl)-2,4-diamino-5-(5'-O-(4',4"-dimethoxytrityl)-2'-deoxy-β-D-ribofuranosyl)-pyrimidine-3'-O-cyanoethdxydiisopropylphophoramidite. $N^2,N^4$-Di-(t-butyl-benzoyl)-2,4-diamino-5-(5'-O-(4',4"-dimethoxytrityl)-2'-deoxy-β-D-ribofuranosyl)-pyrimidine (101 mg; 0.12 mmol) was dissolved in anhydrous acetonitrile (1.3 mL) containing dimethylaminopyridine (10 mg). Diisopropylethylamine (84 μL, 0.48 mmol) was added and the suspension cooled in an ice bath. Cyanoethyldiisopropylchlorophosphoramidite (53 μL, 0.24 mmol) was added dropwise, and the clear solution was shaken at temperature for 15 min. The reaction was stopped by partitioning the mixture between saturated NaHCO$_3$ solution (aqueous, 25 mL) and dichloromethane (25 mL). The combined organic layers were dried over sodium sulfate and the solvents removed by rotary evaporation. The residue was chromatographed (silica, CH$_2$Cl$_2$:EtOAc:TEA 70:30:1) to yield N$^2$,N$^4$-di-(t-butyl-benzoyl)-2,4-diamino-5-(5'-O-(4',4''-cyanoethoxydiisopropylphophoramidite (110 mg, 90%).

N$^2$,N$^4$-dibenzoyl-2,4-diamino-5-(2'-deoxy-beta-D-ribofuranosyl)pyrimidine. 2,4-Diamino-5-(2',3'-O-isopropylidine-5'-O-trityl-beta-D-ribofuranosyl)pyrimidine (2.1 g, 4.0 mmol) was suspended in dry pyridine (40 mL) under a nitrogen atmosphere and treated with benzoyl chloride (4.6 mL, 40 mmol). The mixture became orange, and a precipitate of pyridinium hydrochloride formed. The mixture was stirred at RT for 2 h, and then cooled on ice. The reaction was quenched by addition of water (8 mL). After 5 min, aqueous ammonia (25%, 9.6 mL) was added, and the mixture was stirred for an additional 40 min at RT. Solvent was removed under reduced pressure, and the residue was partitioned between EtOAc and water. The organic layer was washed with saturated NaCl solution, dried (Na$_2$SO$_4$), filtered, and concentrated. TLC (silica, EtOAC:hexane 1:1) showed two products, one carrying the 2,4-dibenzolayted pyrimidine (R$_f$=0.43, major), the other carrying the 2,4-tetrabenzoylated pyrimidine (R$_f$=0.6, minor). The mixture was resolved by flash chromatography (silica, EtOAC:hexane 1:1). The tetrabenzyol derivative was resubmitted to the hydrolysis conditions, and additional N$^2$,N$^4$-dibenzoyl-2,4-diamino-5-(2',3'-O-isopropylidine-5'-O-trityl-beta-D-ribofuranosyl)pyrimidine was recovered (combined yield 64%, 1.8 g) as a white solid, and used directly in the next step.

N$^2$,N$^4$-Dibenzoyl-2,4-diamino-5-(2',3'-O-isopropylidine-5'-O-trityl-beta-D-ribofuranosyl)pyrimidine (1.2 g, 1.6 mmol) was dissolved in 10% methanolic HCl. The mixture was stirred at RT for 1 h. Nitrogen was then bubbled through the solution for 15 min, and the solvents removed by rotary evaporation. The residue was chromatographed (silica, CHCl$_3$:MeOH 11:2) to yield N$^2$,N$^4$-dibenzoyl-2,4-diamino-5-(beta-D-ribofuranosyl)pyrimidine (471 mg, 65%) as a white foam.

N$^2$,N$^4$-Dibenzoyl-2,4-diamino-5-(beta-D-ribofuranosyl)pyrimidine (3.0 mmol) was coevaporated three times from pyridine to remove traces of water, and the residue dried under high vacuum overnight. The residue was then dissolved in anhydrous pyridine (9 mL) and the solution was treated with ClSi(O-2-propyl)$_2$-OSi(O-2-propyl)$_2$-Cl (TPDSC) (3.3 mmol). The mixture was stirred at RT under Ar for 4 h, the pyridine was removed by rotary evaporation, and the residue was partitioned between chloroform and water. The organic layer was washed with water (2×50 mL), dried (Na$_2$SO$_4$), filtered and evaporated. N$^2$,N$^4$-Dibenzoyl-2,4-diamino-5-(3',5'-O-(tetraisopropyldisiloxanyl))-beta-D-ribofuranosyl)pyrimidine was purified by chromatography on silica gel (hexane:EtOAC 9:1). A portion of this compound (2.6 mmol) was dissolved in dry dimethylformamide (6 mL), and the solution was treated with N,N'-thiocarbonyldiimidazole (6.7 mmol). The mixture was stirred at RT (4 h), the mixture was partitioned between EtOAc and water (1:1, total volume 125 mL). The phases were separated, the organic phase washed with water (5×25 mL), dried (Na$_2$SO$_4$), and rotary evaporated to yield. N$^2$,N$^4$-dibenzoyl-2,4-diamino-5-(2'-O(1-imidazoyl-1-yl)thiocharbonyl)-3',5'-O-(tetraisopropyldisiloxanyl))-beta-D-ribofuranosyl)pyrimidine which was purified by chromatography (silica, hexane:EtOAc 9:1). A portion of this compound (1.9 mmol) was dissolved in toluene (19 mL), and the mixture was treated with 2,2'-azobis(2-methylpropionitrile) (1.28 mmol) and tributyltin hydride (7.68 mmol) in toluene (19 mL). The mixture was degassed by purging with oxygen-free argon (40 min), and then heated at 80° C. (3 h). The solvent was then removed by rotary evaporation, and the resulting N$^2$,N$^4$-dibenzoyl-2,4-diamino-5-(2'-deoxy-beta-D-ribofuranosyl)pyrimidine purified by chromatography (silica, elute first with hexane, then with hexane.

EXAMPLE 6

N-Benzyloxycarbonyl-2-[(5'-O-tert-butyl-dimethylsilyl-2',3'-O-isopropylidene)-β-D-ribofuranosyl]-glycine methyl ester. Potassium-tert-butoxide (1.557 g, 13.87 mmol) was suspended at −78° C. in dichloromethane (20 ml). The phosphonate (CH$_3$O)$_2$PO—CH(NH-Cbz)COOCH$_3$ (4.596 g, 13.87 mmol) in dichloromethane (12 ml) was then injected. After ca. 1 h stirring, the cooling bath was replaced with a ice bath and 5'-tertbutyldimethylsilyl-2',3'-isopropylideneribofuranoside (3.52 g, 11.56 mmol) in dichloromethane (23 ml) added dropwise over a period of 1 h slowly. The reaction was stirred first for 6 h at 0° C., then at RT overnight. For the work-up, the mixture was diluted with dichloromethane (ca. 150 ml), the organic phase was washed with satd. aq. sodium chloride (2×80 ml), dried (MgSO$_4$), and filtered. The crude product was adsorbed on silica gel (13 g). Chromatography (silica gel, ether/hexane 2:8, then 4:6) gave, in addition to a small fraction of starting material (ca. 5%), and N-benzyloxycarbonyl-2-[(5'-O-tert-butyl-dimethylsilyl-2',3'-O-isopropylidene)-β-D-ribofuranosyl]-glycine methyl ester (5.313 g, 90%, ca. 3:2) as colorless oil. A third product, presumably the α-anomer, was isolated in small amounts (<3%).

Isomer 1. R$_f$=0.36 (hexane/diethylether 7:3). GCMS: (P1001020) R$_t$=20.2 min; m/z (%)=452; 394; 344; 287; 213; 171; 117; 91 (100). $^1$H-NMR (400 MHz, CDCl$_3$): δ=0.03 (s, 3H, Si—CH$_3$); 0.05 (s, 3H, Si—CH$_3$); 0.84 (s, 9H, SiC(CH$_3$)$_3$); 1.33 (s, 3H, acetonide-CH$_3$); 1.53 (s, 3H, acetonide-CH$_3$); 3.72 (dd, J=2.4, J$_{gem}$=11.4, 1H, 5'$^1$-H); 3.76 (s, 3H, OCH$_3$); 3.83 (dd, J=2.6, J$_{gem}$=11.4, 1H, 5'$^2$-H); .3.97 (m, 1H, 4'-H); 4.52–4.66 (m, 4H, 2'-H, 3'-H, 1'-H, 2-H); 5.12 (s, 1H of CH$_2$Ph); 5.13 (s, 1H of CH$_2$Ph); 5.82 (d, J=9.5, 1H, NH); 7.30–7.37 (m, 5H, arom. phenyl-H). $^{13}$C-NMR (100 MHz, CDCl$_3$): δ=−5.52 (q, Si—CH$_3$); −5.42 (q, Si—CH$_3$); 18.52 (s, SiC(CH$_3$)$_3$); 25.55 (q, acetonide-CH$_3$); 25.94 (q, SiC(CH$_3$)$_3$); 27.60 (acetonide-CH$_3$); 52.55 (q, OCH$_3$); 55.87 (d, N-CH—CO$_2$CH$_3$); 62.98 (t, C-5'); 67.20 (t, OCH$_2$-Ph); 80.32, 82.01, 83.30, 84.97 (4d, C-1', C-2', C-3', C-4'); 113.93 (s, acetonide-C(CH$_3$)$_2$); 128.12, 128.36, 128.39 (3d, phenyl-CH); 136.12 (s, phenyl-C); 156.75 (s, NHCO$_2$CH$_2$Ph); 170.32 (s, CO$_2$CH$_3$). MS: m/z (%)=509.2 (<1, M$^+$); 452 (17, M$^+$-C(CH$_3$)$_3$); 287 (14); 129 (10); 91 (100); 73 (10). IR (CHCl$_3$): ν=3420, 2990, 2950, 2930, 2900, 2860, 1755, 1725, 1510; 1470, 1460, 1455, 1435, 1385, 1375, 1335, 1290, 1260, 1230, 1170, 1155, 1135, 1115, 1080, 1030, 1005, 975, 910, 885, 855, 840, 815, 700.

Isomer 2: R$_f$=0.33 (hexane/diethylether 7:3) GCMS (P1001020) R$_t$=21.5 min; m/z (%)=452; 408; 394; 344; 287; 213; 171; 117; 91 (100).$^1$H-NMR (CDCl$_3$): δ=0.07 (2s, 6H, Si(CH$_3$)$_2$); 0.89 (s, 9H, SiC(CH$_3$)$_3$); 1.33 (s, 3H, acetonide-CH$_3$); 1.51 (s, 3H, acetonide-CH$_3$); 3.68–3.76 (m, 5H, OCH$_3$, 5'$^1$-H, 5'$^2$-H); 4.06–4.11 (m, 2H, 2-H, 4'-H$^{*1}$); 4.51–4.61 (m, 2H, 1'-H$^{*1}$, 3'-H$^{*2}$); 4.70–4.74 (m, 1H, 2'-H$^{*2}$); 5.11 (s, 2H, CH$_2$Ph); 5.51 (d, br., J=5.9, 1H, NH); 7.30–7.36 (m, 5H, phenyl-H).

N-Benzyloxycarbonyl-2-[(5'-O-tert-butyl-dimethylsilyl-2',3'-O-isopropylidene)-β-D-ribofuranosyl]-glycine amide. A solution of N-benzyloxycarbonyl-2-[(5'-O-tert-butyl-dimethylsilyl-2',3'-O-isopropylidene)-β-D-ribofuranosyl]-glycine methyl ester (8.715 g, 17.1 mmol) in methanol (35 ml) was saturated in a glass ampule at 0° C. with ammonia gas. The ampule was sealed and the mixture was stirred at RT ca. 74 h. After concentration, adsorption of the crude product on silica gel and chromatography (silica gel, diethylether/hexane 8:2, later ethyl acetate/hexane 1:1), products N-benzyloxycarbonyl-2-[(5'-O-tert-butyl-dimethylsilyl-2',3'-O-isopropylidene)-b-D-ribofuranosyl]-glycine amide (7.788 g, 92%) were obtained as colorless oil. Diastereomers only be only partly separated. Isomer 1: R$_f$=0.23 (diethylether/hexane 8:2). $^1$H-NMR (CDCl$_3$): δ=0.06 (s, 6H, Si(CH$_3$)$_2$); 0.87 (s, 9H, SiC(CH$_3$)$_3$); 1.32 (s, 3H, acetonide-CH$_3$); 1.52 (s, 3H, acetonide-CH$_3$); 3.73 (dd, J=2.0, J$_{gem}$=11.3, 1H, 5'$^1$-H); 3.91 (dd, J=2.4, J$_{gem}$=11.3, 1H, 5'$^2$-H); 3.95 (m, 1H, 2-H$^{*1}$); 4.46 (m, 2H, 1'-H$^{*1}$, 4'-H$^{*1}$); 4.53 (m, 1H, 3'-H$^{*2}$); 4.64 (dd, J$_1$=4.9, J$_2$=6.4, 1H, 2'-H$^{*2}$); 5.12, 5.14 (2s, je 1H, CH$_2$Ph); .5.82 (s, br., 1H of CONH$_2$); 6.00 (bd, J=6.6, 1H, PhCH$_2$OCONH); 6.57 (s, br., 1H of CONH$_2$); 7.30–7.37 (m, 5H, arom. phenyl-H). $^{13}$C-NMR (CDCl$_3$): δ=-5.38 (q, Si(CH$_3$)$_2$); 18.58 (s, SiC(CH$_3$)$_3$); 25.57 (q, acetonide-CH$_3$); 26.01 (q, SiC(CH$_3$)$_3$); 27.55 (acetonide-CH$_3$); 55.64 (d, N-CH—CONH$_2$); 62.49 (t, SiOCH$_2$); 67.33 (t, OHC$_2$-Ph); 79.87, 81.74, 82.77, 84.48 (4d, C-1', C-2', C-3', C-4'); 114.53 (s, acetonide-C(CH$_3$)$_2$); 128.28, 128.51 (2d, phenyl-CH); 136.02 (s, phenyl-C; 156.38 (s, NHCO$_2$CH$_2$Ph); 171.46 (s, CONH$_2$). MS: m/z (%)=494.5 (2, M$^+$); 479.5 (1, M$^+$-CH$_3$); 450.5 (5, M$^+$-CONH$_2$); 437 (7, M$^+$-C(CH$_3$)$_3$); 406 (5); 379 (3); 348 (5); 287 (7, M$^+$-1'-Substituent); 171 (6); 129 (9); 117 (8); 101 (5); 97 (6); 92 (9); 91 (100); 75 (13); 73 (17); 59 (12); 57 (12); 43 (19). IR (CHCl$_3$): ν=3520, 3480, 3400, 3340, 3000, 2990, 2950, 2930, 2890, 2860, 1725, 1695, 1585, 1575, 1500, 1470, 1465, 1455, 1415, 1385, 1375, 1325, 1310, 1255, 1160, 1125, 1080, 1030, 1015, 980, 855, 835, 815, 700.

Isomer 2. R$_f$=0.29 (diethylether/hexane 8:2). $^1$H-NMR: (CDCl$_3$): δ=0.12 (s, 3H, Si—CH$_3$); 0.13 (s, 3H, Si—CH$_3$); 0.91 (s, 9H, SiC(CH$_3$)$_3$); 1.30 (s, 3H, acetonide-CH$_3$); 1.51 (s, 3H, acetonide-CH$_3$); 3.73 (dd. J=4.9, J$_{gem}$=11.5, 1H, 5'$^1$-H); 3.83 (dd, J=3.3, J$_{gem}$=11.5, 1H, 5'$^2$-H); 4.01 (dd, J$_1$=2.7, J$_2$=9.9, 1H, 2-H$^{*1}$); 4.18–4.26 (m, 2H, 4'-H, 1'-H$^{*1}$); 4.64–4.66 (m, 1H, 3'-H$^{*2}$); 4.81–4.84 (m, 1H, 2'-H$^{*2}$); 5.12 (s, 2H, CH$_2$Ph); 5.50 (s, br., 1H of CONH$_2$); 5.72 (s, br., 1H, PhCH$_2$OCONH); 6.73 (s, br., 1H of CONH$_2$); 7.30–7.37 (m, 5H, arom, phenyl-H). $^{13}$C-NMR (CDCl$_3$): δ=-5.40 (q, Si—CH$_3$); -5.31 (q, Si—CH$_3$); 18.48 (s, SiC(CH$_3$)$_3$); 25.48 (q, acetonide-CH$_3$); 25.93 (q, SiC(CH$_3$)$_3$); 27.29 (acetonide-CH$_3$); 55.65 (d, N-CH—CONH$_2$); 63.81 (t, SiOCH$_2$); 67.20 (t, OCH$_2$-Ph); 81.22, 83.35, 85.49, 86.37 (4d, C-1', C-2', C-3', C4'); 113.56 (s, acetonide-C(CH$_3$)$_2$); 127.99, 128.16, 128.51 (3d, phenyl-CH); 136.12 (s, phenyl-C); 156.67 (s, NHCO$_2$CH$_2$Ph); 171.44 (s, CONH$_2$).

2-(5'-tert.-Butyldimethylsilyl-2',3'-O-isopropylidene-β-D-ribofuranosyl)-N-Cbz-D,L-glycinnitrile. 2-(5'-tert.-Butyldimethylsilyl-2',3'-O-isopropylidene-β-D-ribofuranosyl)-N-Cbz-D,L-glycine amide (21.7 g, 43.9 mmol) was dissolved in abs. dioxane (400 mL). Pyridine (10.6 mL, 131.7 mmol) was added and the resulting solution cooled to 10° C. Trifluoroacetic acid anhydride (10.5 mL, 74.6 mmol) was injected and the solution afterwards warmed to RT and stirred for 14 h. The solution was diluted with CHCl$_3$ and extracted with ice/H$_2$O, H$_2$O and sat. aq. NaCl soln. The organic phase was dried over MgSO$_4$ and the solvents removed under vacuum to yield 2-(5'-tert.-butyldimethylsilyl-2',3'-O-isopropylidene-β-D-ribofuranosyl)-N-Cbz-D,L-glycinnitrile (22.53 g, quantitative) as a brown oil, which was used directly for the next reaction. MS m/z (rel intensity) 477 (M$^+$+1; 1), 476 (M$^+$; 1), 311 (59), 302 (52), 258 (62), 117 (59), 108 (57), 92 (53), 91 (100), 89 (54), 79 (51), 75 (64), 73 (67), 59 (54), 43 (64); IR (CHCl$_3$): 3430, 2960, 2930, 2860, 1730, 1500, 1375, 1285, 1260, 1130, 1080, 805, 785; $^1$H-NMR (CDCl$_3$): The signals of the two diastereomeric compounds formed in a 2:1 ratio could be assigned via COSY-spectroscopy (major product=a; minor product=b). 0.04 and 0.05 (s, 3H, Me$_a$—Si—Me$_a$), 0.10 (s, 6H, Me$_b$-Si—Me$_b$), 0.84 (s, 9H, tBu$_a$), 0.91 (s, 9H, tBu$_b$), 1.32 and 1.52 (s, 3H, Me$_a$—C—Me$_a$), 1.34 and 1.52 (s, 3H, Me$_b$—C—Me$_b$), 3.74 (dd, J=23.9, 11.2, 1H, Hα-C(5'$_b$)), 3.76 (dd, J=2.2, 11.4, 1H, Hα-C(5'$_a$)), 3.79 (dd, J=3.5, 11.2, 1H, Hβ-C(5'$_b$)), 3.90 (dd, J=2.5, 11.4, 1H, Hβ-C(5'$_a$)), 4.07 (dd, J=4.3, 6.0, 1H, H—C(1'$_b$)), 4.12 (m, 1H, H—C(4'$_a$)), 4.18 (m, 1H, H—C(4'$_b$)), 4.29 (br., 1H, H—C(1'$_a$)), 4.48 (dd, J=5.8, 5.9, 1H, H—C(2'$_a$)), 4.57 (dd, J=4.4, 6.4, 1H, H—C(2'$_b$)), 4.67 (dd, J=3.6, 6.2, 1H, H—C(3'$_a$)), 4.70 (dd, J=3.0, 6.5, 1H, H—C(3'$_b$)), 4.87 (d-br., J=8.0, 2H, methine H$_{a+b}$)), 5.10–5.17 (m, 4H, methylen H$_{a+b}$), 5.42 (d-br., J=8.0, 1H, NH$_b$), 5.93 (d-br., J=9.0, 1H, NH$_a$), 7.31–7.38 (m, 10H, arom. H$_{a+b}$)); $^{13}$C-NMR (CDCl$_3$): -5.45 and -5.34 (q, Me$_b$—Si—Me$_b$), -5.42 and -5.38 (q, Me$_a$—Si—Me$_a$), 18.50 (s, tBu$_b$), 18.59 (s, tBu$_a$), 25.37 and 27.30 (q, Me$_b$—C—Me$_b$), 25.47 and 27.52 (q, Me$_a$—C—Me$_a$), 26.00 (q, tBu$_{a+b}$)), 45.06 (d, methine C$_a$), 45.88 (d, methine C$_b$), 63.38 (t, C(5'$_b$)), 63.80 (t, C(5'$_a$)), 67.89 (t, methylen C$_b$), 68.00 (t, methylen C$_a$), 80.88, 82.26, 83.92 and 85.92 (d, C(1'$_b$), C(2'$_b$), C(3'$_b$) and C(4'$_b$)), 81.32, 82.03, 83.17 and 85.47 (d, C(1'$_a$), C(2'$_a$), C(3'$_a$) and C(4'$_a$)), 114.32 (s, Me$_a$C-Me$_a$), 114.43 (s, Me$_b$—C—Me$_b$), 116.53 (s, CN$_b$), 116.99 (s, CN$_a$), 128.34 and 128.53 (d, arom. C(2'$_b$) and arom. C(3'$_b$)), 128.74 (d, arom. C(4'$_b$)), 135.42 (s, arom. C(1'$_a$)), 135.50 (s, arom. C(1'$_b$)), 155.47 (s, carbamate C$_b$), 155.57 (s, carbamate C$_b$).

2-Amino-3-(5'-tert.-butyldimethylsilyl-2',3'-O-isopropylidene-β-D ribofuranosyl)-5-methylpyrazin-1-oxide. 2-(5'-tert.-Butyldimethylsilyl-2',3'-O-isopropylidene-β-D-ribofuranosyl)-N-Cbz-D,L-glycinnitrile (100 mg, 0.21 mmol) was dissolved in dioxane (2 mL). 10% Pd—C (10 mg) was added and the suspension stirred at RT in an H$_2$-atmosphere over night. The Pd—C was removed by centrifugation. Anti-methylglyoxal-1-oxime (27 mg, 0.31 mmol) was added, the solution heated to reflux for 54 h and the solvent evaporated. Chromatography (silica gel, EtOAc/hexane 8:2) yielded 2-amino-3-(5'-tert.-butyldimethylsilyl-2',3'-O-isopropylidene-β-D ribofuranosyl)-5-methylpyrazin-1-oxide (40 mg, 46% for two steps) as a brown oil. A larger scale reaction (23 mmol) proceeded analogously. MS m/z (rel intensity) 411 (M$^+$; 1), 208 (92), 150 (55), 134 (57), 133 (71), 117 (53), 75 (100), 73 (99); IR (CHCl$_3$): 3430, 3320, 2990, 2960, 2930, 2860, 1610, 1565, 1490, 1385, 1335, 1260, 1140, 1105, 1080, 985, 860, 840; $^1$H-NMR (CDCl$_3$): 0.06 (s, 3H, Me—Si), 0.09 (s, 3H, Me—Si), 0.83 (s, 9H, tBu), 1.39 (s, 3H, Me$_2$C), 1.62 (s, 3H, Me$_2$C, 2.37 (s, 3H, Me—C(5)); 3.82 (dd, J=2.3, 11.3, 1H, H—C(5a')), 3.91 (dd, J=2.6, 11.3, 1H, H—C(5b')), 4.24 (m, 1H, H—C(4')), 4.83 (dd, J=3.6, 6.5, 1H, H—C(3')), 5.02–5.09 (m, 2H, H—C(1') and H—C(2')), 6.28 (s, 2H, NH$_2$), 7.87 (s, 1H, H—C(6)); $^{13}$C-NMR (CDCl$_3$): -5.53 (q, Me$_2$Si), 18.48 (s, tBu), 20.52 (q, Me—C(5)), 25.48 (q, Me$_2$C), 25.90 (q, tBu), 27.45 (q, Me$_2$C), 62.81 (t, C(5')), 80.99, 82.93, 85.24 and 87.40 (d, C(1'), C(2'), C(3') and C(4')), 114.88 (s, Me$_2$C), 129.13 (d, C(6)), 139.45, 141.26 and 143.59 (s, C(2), C(3) and C(5)).

2-Acetoxy-5-(51-tert.-butyldimethylsilyl-2',3'-O-isopropylidene-β-D-ribofuranosyl)-6-diacetylamino-3-methylpyrazine. 2-Amino-3-(5'-tert.-butyldimethylsilyl-2',3'-O-isopropylidene-β-D-ribofuranosyl)-5-methylpyrazin-1-oxide (2.27 g, 5.51 mmol) was dissolved in acetic acid anhydride (2.0 mL). KOAc (0.54 g, 5.51 mmol) was added and the resulting suspension heated to reflux for 9 min. The mixture was cooled to RT, and the anhydride removed under reduced pressure. To remove last traces of anhydride, the resulting brown oil was dissolved in EtOH and the solvent evaporated. The crude product was dissolved in CH$_2$Cl$_2$, and excess KOAc removed by filtration. The product was adsorbed on silica gel by addition of silica gel (8 g) and evaporation of the solvent. Chromatography (silica gel (200 g), Et2O/hexane 4:6) yielded 2-acetoxy-5-(5'-tert.-butyldimethylsilyl-2',3'-O-isopropylidene-β-D ribofuranosyl)-6-diacetylamino-3-methylpyrazine (1.96 g, 66%) as a slightly yellow oil. MS m/z (rel intensity) 537 (M$^+$; 1), 75 (63), 73 (66), 43 (100); IR (CHCl$_3$): 2960, 2930, 2860, 1790, 1770, 1725, 1420, 1370, 1260, 1170, 1140, 1075, 840; $^1$H-NMR (CDCl$_3$): 0.02 (s, 3H, Me$_2$Si), 0.01 (s, 3H, Me$_2$Si), 0.83 (s, 9H, tBu), 1.38 (s, 3H, Me$_2$C), 1.56 (s, 3H, Me$_2$C), 2.09 (s-br., 3H, N—Ac), 2.38 (s, 3H, Me—C(3) oder O—Ac), 2.49 (s-br., 3H, N—Ac), 2.54 (s, 3H, Me—C(3) oder O—Ac), 3.66 (AB-system, 2H, H—C(5')), 4.19 (m, 1H, H—C(4')), 4.75 (dd, J=3.2, 6.3, 1H, H—C(3')), 4.93 (d, J=4.2, 1H, H—C(1')), 5.22 (dd, J=4.2, 6.3, 1H, H—C(2')); $^{13}$C-NMR (CDCl$_3$): −5.74 (q, Me$_2$Si), −5.41 (q, Me$_2$Si), 18.29 (s, tBu), 19.03 (q, Me—C(3)), 20.85 (q, O—Ac), 25.61 (q, Me$_2$C), 25.84 (q, tBu), 26.45 (q, N—Ac), 26.90 (q, N—Ac), 27.58 (q, me$_2$C), 63.42 (t, C(5')), 82.22, 82.48, 83.42 and 85.98 (d, C(1'), C(2'), C(3') and C(4')), 113.88 (s, me$_2$C), 143.37, 147.68, 149.23 and 151.40 (s, C(2), C(3), C(5) and C(6)), 168.01 (s, O—Ac), 171.88 (s, N—Ac), 172.73 (s, N—Ac).

6-Amino-5-(5'-tert.-butyldimethylsilyl-2',3'-O-isopropylidene-β-D-ribofuranosyl)-3-methylpyrazin-2-one. 2-Acetoxy-5-(5'-tert.-butyldimethylsilyl-2',3'-O-isopropylidene-β-D-ribofuranosyl)-6-diacetylamino-3-methylpyrazine (100 mg, 0.19 mmol) was dissolved in hydrazine hydrate (1 mL) and the mixture was stirred for 2 h at RT. The solution was cooled to 0° C. and cautiously neutralized to pH 7 with 2 N aq. HCl soln. An oil separated which after trituration with H$_2$O yielded 6-amino-5-(5'-tert.-butyldimethylsilyl-2',3'-O-isopropylidene-β-D-ribofuranosyl)-3-methylpyrazin-2-one (62 mg, 80%) as a yellow solid. FAB-MS (3-NOBA): 412 (M$^+$+1); $^1$H-NMR (CDCl$_3$): 0.05 (s, 3H, Me$_2$Si), 0.07 (s, 3H, Me$_2$Si), 0.88 (s, 9H, tBu), 1.37 (s, 3H, Me$_2$C), 1.59 (s, 3H, Me$_2$C), 2.25 (s, 3H, Me—C(3)), 3.76 (dd, J=2.9, 11.2, 1H, Ha-C(5')), 3.85 (dd, J=3.1, 11.2, 1H, Hb-C(5')), 4.10 (m, 1H, H—C(4')), 4.76 (dd, J=3.7, 6.8, 1H, H—C(3')), 4.92 (d, J=5.0, 1H, H—C(1')), 5.03 (dd, J=5.1, 6.7, 1H, H—C(2')), 5.61 (s, 2H, br., NH$_2$); $^{13}$C-NMR (CDCl$_3$):−5.32 (q, Me$_2$Si), −5.28 (q, Me$_2$Si), 18.7 (s, tBu), 18.8 (q, Me—C(3)), 25.9 (q, Me$_2$C), 26.1 (q, tBu), 27.9 (q, Me$_2$C), 63.3(t, C(5')), 81.2, 83.2, 84.9 and 86.6 (d, C(1'), C(2'), C(3') and C(4')), 114.8 (s, Me$_2$C), 117.0, 136.2, 143.2 and 157.0 (s, C(2), C(3), C(5) and C(6)).

6-Acetylamino-5-(5'-tert.-butyldimethylsilyl-2',3'-O-isopropylidene-β-D-ribofuranosyl)-3-methylpyrazin-2-one. 2-Acetoxy-5-(5'-tert.-butyldimethylsilyl-2',3'-O-isopropylidene-β-D-ribofuranosyl)-6-diacetylamino-3-methylpyrazine (294 mg, 0.55 mmol) was dissolved in MeOH (6 mL), conc. aq. NH$_3$ soln. (0.1 mL) was added and the resulting solution stirred for 12 min. The solvent was then evaporated and the crude product was adsorbed on silica gel. Chromatography (silica gel (10 g), EtOAc/CH$_2$Cl$_2$=3:2) yielded 6-acetylamino-5-(5'-tert.-butyldimethylsilyl-2',3'-O-isopropylidene-β-D-ribofuranosyl)-3-methylpyrazin-2-one (236 mg, 95%) as amorphous solid. FAB-MS (3-NOBA): 454 (M$^+$+1); $^1$H-NMR (CDCl$_3$): 0.00 (s, 3H, Me$_2$Si), 0.02 (s, 3H, Me$_2$Si), 0.83 (s, 9H, tBu), 1.41 (s, 3H, Me$_2$C), 1.59 (s, 3H, Me$_2$C), 2.18 and 2.38 (s, 2×3H, Me—C(3) and N—Ac), 3.68 (dd, J=4.7, 11.5, 1H, Ha-C(5')), 3.76 (dd, J=3.2, 11.5, 1H, Hb-C(5')), 4.29–4.31 (m, 1H, H—C(4')), 4.63 (dd, J=3.1, 6.5, 1H, H—C(3')), 5.08 (d, J=3.8, 1H, H—C(1')), 5.19 (dd, J=3.8, 6.5, 1H, H—C(2')), 9.67 (s, 1H, br., NH), 12.20 (s, 1H, br., NH); $^{13}$C-NMR (CDCl$_3$):−5.46 (q, Me$_2$Si), −5.44 (q, Me$_2$Si), 18.3 (s, tBu), 20.02 (q, Me—C(3)), 24.95 (q, N—Ac), 25.44 (q, Me$_2$C), 25.77 (q, tBu), 27.36 (q, me$_2$C), 63.54 (t, C(5')), 81.04, 84.54, 85.75 and 86.44 (d, C(1'), C(2'), C(3') and C(4')), 114.07 (s, Me$_2$C), 114.69, 133.59, 150.14 and 153.84 (s, C(2), C(3), C(5) and C(6)), 171.05 (s, N—Ac); Anal. calc. for C$_{21}$H$_{35}$N$_3$O$_6$Si (453.61): C, 55.61, H, 7.78, N, 9.26; found: C, 55.50, H, 7.86, N, 9.06.

6-Acetylamino-2-benzyloxy-5-(5'-tert.-butyldimethylsilyl-2',3'-O-isopropylidene-β-D-ribofuranosyl)-3-methylpyrazine. 6-Acetylamino-5-(5'-tert.-butyldimethylsilyl-2',3'-O-isopropylidene-β-D-ribofuranosyl)-3-methylpyrazin-2-one (468 mg, 1.03 mmol) and triphenylphosphine (406 mg, 1.55 mmol) were dried for 1.5 h at 50° C. under high vacuum and then dissolved in abs. THF (9 mL). Benzyl alcohol (128 μL, 1.24 mmol) was added and the resulting homogenous solution cooled to 0° C. DEAD (243 μL, 1.55 mmol) was slowly added over a period of 10 min. After being stirred for 30 min. at 0° C., the solution was cooled in N$_2$(1) and the solvent removed under high vacuum at low temperature. Chromatography (silica gel (60 g), EtOAc/hexane 10:90 then 20:80 then 25:75 then 30:70) yielded 6-acetylamino-2-benzyloxy-5-(5'-tert.-butyldimethylsilyl-2',3'-O-isopropylidene-β-D-ribofuranosyl)-3-methylpyrazine (382 mg, 68%) as amorphous foam. FAB-MS (3-NOBA): 544 (M$^+$+1); $^1$H-NMR (CDCl$_3$): −0.10 (s, 3H, Me$_2$Si), −0.05 (s, 3H, Me$_2$Si), 0.79 (s, 9H, tBu), 1.41 (s, 3H, Me$_2$C), 1.59 (s, 3H, Me$_2$C), 2.30 and 2.45 (s, 2×3H, Me—C(3) and N—Ac), 3.59 (dd, J=4.5, 11.1, 1H, Ha-C(5')), 3.63 (dd, J=4.3, 11.1, 1H, Hb-C(5')), 4.26–4.28 (m, 1H, H—C(4')), 4.72 (dd, J=2.7, 6.5, 1H, H—C(3')), 5.07 (d, J=4.1, 1H, H—C(1')), 5.38 (s, 2H, CH$_2$-Bn), 5.45 (dd, J=4.1, 6.5, 1H, H—C(2')), 7.31–7.43 (m, 5H, arom. H), 8.71 (s, 1H, br., NH); $^{13}$C-NMR (CDCl$_3$): −5.56 (q, Me$_2$Si), −5.54 (q, Me$_2$Si), 18.28 (s, tBu), 18.56 (q, Me—C(3)), 24.56 (q, N—Ac), 25.56 (q, Me$_2$C), 25.78 (q, tBu), 27.43 (q, me$_2$C), 63.47 (t, C(5')), 68.18 (t, CH$_2$-Bn), 81.91, 82.76, 84.45 and 85.82 (d, C(1'), C(2'), C(3') and C(4')), 113.80 (s, Me$_2$C), 127.58, 127.99 and 128.52 (d, arom. CH), 136.63 (s, Bn), 132.54, 137.43 and 141.7 (s, C(2), C(3), C(5) and C(6)), 155,75 (s, N—Ac); Anal. calc. for C$_{28}$H$_{41}$N$_3$O$_6$Si (543.74): C 61.85, H 7.60, N 7.73; found: C 62.12, H 7.82, N 7.88.

6-Amino-2-benzyloxy-3-methyl-5-β-D-ribofuranosyl-pyrazine. 6-Acetylamino-2-benzyloxy-5-(5'-tert.-butyldimethylsilyl-2',3'-O-isopropylidene-β-D-ribofuranosyl)-3-methylpyrazine (147 mg, 0.27 mmol) was dissolved in MeOH/HCl (2% HCl, 1.5 mL) at RT and stirred for 3.75 h. Solid NaHCO$_3$ was added until the production of CO$_2$(g) ceased. The inorganic salts were removed by filtration and the solvent evaporated. Chromatography (silica gel (115 g), CH$_2$Cl$_2$/MeOH 25:1 then 20:1 then 15:1) yielded 6-amino-2-benzyloxy-3-methyl-5-β-D-ribofuranosylpyrazine (56 mg, 60%) as a white solid. To obtain an analytical sample for the final step, the product was recrystallized from CH$_3$CN. M.p. 152–153° C.; FAB-MS (3-NOBA): 348 (M$^+$+1); $^1$H-NMR (CD$_3$OD): 2.27 (s, 3H, Me—C(3)), 3.72 (dd, J=2.8, 11.9, 1H, Ha-C(5')), 3.85 (dd, J=2.8, 11.9, 1H, Hb-C(5')), 3.98–4.01 (m, 1H, H—C(4')), 4.19 (dd, J=4.5, 5.7, 1H, H—C(3')), 4.31–4.35 (triplettoide m, 1H, H—C(2')), 4.82 (d, J=6.4, 1H, H—C(1')), 5.34 (s, 2H, CH$_2$-Bn), 7.28–7.45 (m, 5H, arom. H); $^{13}$C-NMR (CD$_3$OD): 17.21 (q, Me—C(3)), 62.91 (t, C(5')), 68.52 (t, CH$_2$-Bn), 72.53, 74.71, 84.34 and 86.64 (d, C(1'), C(2'), C(3') and C(4')), 128.85, 128.92 and 129.45 (d, arom. CH), 138.78 (s, Bn), 128.11, 129.26, 151.73 and 157.83 (s, C(2), C(3), C(5) and C(6)); Anal. calc. for C$_{17}$H$_{21}$N$_3$O$_5$ (347.4): C 58.78, H 6.09, N 12.10; found: C 59.01, H 6.11, N 12.03.

6-Amino-3-methyl-5-(β-D-ribofuranosyl)-pyrazin-2-one. 6-Amino-2 benzyloxy-3-methyl-5-(β-D-ribofuranosylpyrazine (21 mg, 0.060 mmol) was dissolved in MeOH (3 mL) at RT and the solution cooled to 0° C. PdOH—C was added and the suspension stirred under H$_2$(g) for 1 h at 0° C. The catalyst was quickly removed by filtration and the product containing solution recovered in a precooled flask. The resulting colorless solution was cooled in N$_2$(l). Evaporation of the solvent at low temperature under high vacuum yielded 6 amino-3-methyl-5-(β-D-ribofuranosyl)-pyrazin2-one (18 mg, quant.) as amorphous white solid. Dissolution of the crude product at RT in H$_2$O followed by addition of CH$_3$CN and cooling yielded a few mg of crystalline material. The rest of the material was recovered as amorphous solid after evaporation of the solvent. M.p. 165° C. (dec.); FAB-MS (glycerin): 258 (M$^+$+1); IR (KBr): 3.420 (br.), 3930, 1625 (br.), 1540, 1475, 1375, 1160 (sh), 1075 (br.), 960, 795; $^1$H-NMR (DMSO): 2.07 (s, 3H, Me—C(3)), 3.40–3.58 (m, 2H, Ha-C(5') and Hb-C(5')), 3.75–3.78 (quadruplettoide m, 1H, H—C(4')), 3.95 (s, very br., 1H, H—C(3')), 4.16–4.17 (quadruplettoide m, 1H, H—C(2')), 4.60 (d, J=6.7, 1H, H—C(1')), 4.754.79 (m, 2H, HO—C(2') and HO—C(3')), 5.11–5.13 (triplettoide m, br., 1H, HO—C(5')), 5.79 (s, br. 2H, NH$_2$), 11.1 (s, very br., 1H, NH); $^1$H-NMR (D$_2$O): 2.19 (s, 3H, Me—C(3)), 3.79 (dd, J=3.4, 12.5, 1H, Ha-C(5')), 3.84 (dd, J=3.0, 12.5, 1H, Hb-C(5')), 4.07 (ddd, J=3.0, 3.4, 3.7, 1H, H—C(4')), 4.25 (dd, J=3.7, 5.8, 1H, H—C(3')), 4.37 (dd, J=5.8, 7.7, 1H, H—C(2')), 4.79 (d, J=7.7, 1H, H—C(1')); $^{13}$C-NMR (D$_2$O): 19.91 (q, Me—C(3)), 64.06 (t, C(5')), 73.59, 75.42, 82.94 and 87.69 (d, C(1'), C(2'), C(3') and C(4')), 116.97, 141.05, 145.86 and 160.09 (s, C(2), C(3), C(5) and C(6)); Anal. calc. for C$_{10}$H$_{15}$N$_3$O$_5$ (257.25): C 46.69, H 5.88, N 16.33; found: C 46.31, H 5.82, N 15.82.

2-(β-D-Ribofuranosyl)-N-Cbz-D,L-glycinnitrile. 2-(5'-tert.-Butyldimethylsilyl-2',3'-O-isopropylidene-(β-D-ribofuranosyl)-N-Cbz-D,L-glycinnitrile (5.18 g, 10.9 mmol) was dissolved in a mixture of TFA/H$_2$O=4:1, and the mixture stirred for 1 h at RT. The solvent was removed by distillation and last traces of TFA were removed by coevaporation with EtOH. Chromatography (silica gel, CH$_2$Cl$_2$/EtOH 13:1) of the resulting oil yielded 2-(β-D-ribofuranosyl)-N-Cbz-D,L-glycinnitrile (1.80 g, 83%) as two separable oils (first eluting product=diastereomer a). Diastereomer a: MS m/z (rel intensity) 322 (M$^+$; 0.5), 108 (33), 107 (28), 91 (100), 79 (31), 77 (20); $^1$H-NMR (DMSO): 3.38–3.47 (m, 1H, Ha-C(5')), 3.52–3.58 (m, 1H, Hb-C(5')), 3.73–3.77 (m, 1H), 3.80–3.85 (m, 2H) and 3.91–3.94 (m, 1H): H—C(1'), H—C(2'), H—C(3') and H—C(4'), 4.78 (dd, J=4.1, 8.4, 1H, C—H), 4.87 (dd, J=5.1, 5.2, 1H, OH), 4.96 (d, J=4.7, 1H, OH), 5.06 (d, J=5.0, 1H, OH), 5.05–5.15 (m, 2H, CH$_2$), 7.34–7.39 (m, 5H, arom. H), 8.06 (d, J=8.4, 1H, NH); $^{13}$C-NMR (DMSO): 44.56 (d, methine C), 61.31 (t, C(5')), 66.33 (t, methylene C), 70.96, 71.24, 81.65 and 85.01 (d, C(1'), C(2'), C(3') and C(4')), 118.22 (s, CN), 127.89, 128.04 and 128.44 (d, arom. C(2'), arom. C(3') and arom. C(4')), 136.39 (s, arom. C(1')), 155.74 (s, carbamate C). Diastereomer b: MS m/z (rel intensity) 323 (M$^+$+1; 1.2), 322 (M$^+$; 3.0), 108 (28), 107 (21), 97 (17), 92 (17), 91 (100), 79 (17); $^1$H-NMR (DMSO): 3.37–3.51 (m, 2H, Ha-C(5') and Hb-C(5')), 3.74–3.92 (m, 4H, H—C(1'), H—C(2'), H—C(3') and H—C(4')), 4.67 (dd, J=6.1, 8.4, 1H, C—H), 4.74 (dd, J=5.3, 5.4, 1H, OH), 4.96 (d, J=5.4, 1H, OH), 5.08–5.10 (m, 3H, CH$_2$ and OH), 7.33–7.3 (m, 5H, arom. H), 8.34 (d, J=8.4, 1H, NH); $^{13}$C-NMR (DMSO): 45.73 (d, methine C), 61.39 (t, C(5')), 66.21 (t, methylen C), 70.76, 71.32, 81.23 and 84.82 (d, C(1'), C(2'), C(3') and C(4')), 117.74 (s, CN), 127.80, 127.98 and 128.42 (d, arom. C(2'), arom. C(3') and arom. C(4')), 136.48 (s, arom. C(1')), 155.57 (s, carbamate C).

2-(5'-tert.-Butyldiphenylsilyl-β-D-ribofuranosyl)-N-Cbz-D,L-glycinnitrile. 2-β-D-Ribofuranosyl)-N-Cbz-D,L-glycinnitrile (1.63 g, 5.0 mmol) and imidazole (0.68 g, 10.0 mmol) were dissolved in DMF (16.0 mL) and the resulting solution cooled to 0° C. TBDPSCl (1.55 mL, 6.24 mmol) was slowly added over a period of 0.5 h, the solution warmed to RT, and stirred for 3 h. H$_2$O was added and the solution extracted by addition of CH$_2$Cl$_2$. The org. phase was extracted with H$_2$O (2×) and sat. aq. NaCl soln. After drying (MgSO$_4$) the solvent was evaporated to yield crude 2-(5'-tert.-butyldiphenylsilyl-β-D-ribofuranosyl)-N-Cbz-D, L-glycinnitrile. The product was used directly for the next reaction. A reaction with diastereomer b proceeded analogously.

2-(2',3'-Acetyl-5'-tert.-butyldiphenylsilyl-β-D-ribofuranosyl)-N-Cbz-D,L-glycinnitrile. 2-(5'-tert.-Butyldiphenylsilyl-β-D-ribofuranosyl)-N-Cbz-D,L-glycinnitrile from the above reaction was dissolved in a mixture of pyridine (8.1 mL, 100 mmol) and acetic acid anhydride (14.2 mL, 150 mmol) and stirred at RT for 20 h. The solvent was removed by repeated coevaporation with toluene and the resulting oil dried over night under high vacuum. Chromatography (silica gel, EtOAc/hexane 3:7) yielded 2-(2',3'-acetyl-5'-tert.-butyldiphenylsilyl-β-D-ribofuranosyl)-N-Cbz-D,L-glycinnitrile (2.77 g, 82% over 2 steps) as a clear oil. An analogous reaction with the other diastereomer b gave isomeric 2-(2',3'-acetyl-5'-tert.-butyldiphenylsilyl-β-D-ribofuranosyl)-N-Cbz-D,L-glycinnitrile (78% over 2 steps). Diastereomer a: MS m/z (rel intensity) 587 (M$^+$−57[tBu]; 15), 241 (52), 199 (47), 91 (100), IR (CHCl$_3$): 3420 (br.), 2960, 2930, 2890, 2860, 1745 (br.), 1500, 1430, 1370, 1115, 1105, 1055, 930, 905; $^1$H-NMR (CDCl3): 1.00 (s, 9H, tBu), 2.07 (s, 3H, Ac), 2.09 (s, 3H, Ac), 3.77 (dd, J=3.0, 11.7, 1H, Ha-C(5')) 3.91 (dd, J=2.5, 11.7, 1H, Hb-C(5')), 4.08–4.10 (m, 1H, H—C(1') or H—C(4')), 4.27–4.30 (m, 1H, H—C(1') or H—C(4')), 4.92–4.98 (m, 2H, H—C(2') or H—C(3') and methine H), 5.11–5.19 (m, 2H, methylen H), 5.33 (dd, J=4.5, 5.6, 1H, H—C(2') or H—C(3')), 5.49 (d, J=8.7, 1H, NH), 7.24–7.44 and 7.63–7.68 (m, 15H, arom. H); $^{13}$C-NMR (CDCl$_3$): 19.11 (s, tBu), 20.43 and 20.52 (q, Ac), 26.84 (q, tBu), 44.57 (d, methine C), 63.03 (t, C(5')), 67.99 (t, methylen C), 70.71, 71.19, 79.99 and 83.54 (d, C(1'), C(2'), C(3') and C(4')), 116.71 (s, CN), 127.85, 127.91, 127.95, 128.39, 128.53, 129.94, 130.02, 135.45 and 135.68 (d, arom. C(2'), arom. C(3') and arom. C(4')), 132.52, 132.76 and 135.36 (s, arom.

C(1')), 155.38 (s, carbamate C), 169.56 and 169.67 (s, Ac). Diastereomer b: MS m/z (rel intensity) 645 (M$^+$+1; 3.3), 587 (M$^+$−57[tBu]; 17), 135 (31), 91 (100); IR (CHCl$_3$): 3430 (br.), 2960, 2930, 2890, 2860, 1745 (br.), 1500, 1430, 1375, 1115, 1105, 1060, 1020, 980, 940; $^1$H-NMR (CDCl$_3$): 1.06 (s, 9H, tBu), 2.07 (s, 3H, Ac), 2.08 (s, 3H, Ac), 3.76 (dd, J=3.9, 11.6, 1H, Ha-C(5')), 3.82 (dd, J=3.6, 11.6, 1H, Hb-C (5')), 4.06–4.13 (m, 2H, H—C(1') and H—C(4')), 4.83–5.00 (m, 1H, methine H), 5.06 (d, J=12.0, 1H, methylen Ha), 5.13 (d, J=12.0, 1H, methylen Hb), 5.20 (d, J=5.8, 7.2, 1H, H—C(2') or H—C(3')), 5.40 (d, J=4.0, 5.8, 1H, H—C(2') or H—C(3')), 5.52 (d, J=7.8, 1H, NH), 7.31–7.44 and 7.64–7.69 (m, 15H, arom. H); $^{13}$C-NMR (CDCl$_3$): 19.14 (s, tBu), 20.45 and 20.56 (q, Ac), 26.83 (q, tBu), 44.97 (d, methine C), 63.23 (t, C(5')), 67.92 (t, methylen C), 77.38, 71.68, 79.48 and 83.53 (d, C(1'), C(2'), C(3') and C(4')), 115.61 (s, CN), 127.85 (double intensity), 128.36, 128.49, 128.60, 129.86, 129.91, 135.65 and 135.67 (d, arom. C(2'), arom. C(3') and arom. C(4')), 132.72, 132.80 and 137.47 (s, arom. C(1')), 155.07 (s, carbamate C). 169.51 and 169.89 (s, Ac).

2-(2',3'-Acetyl-5'-tert.-butyldiphenylsilyl-β-D-ribofuranosyl)-D,L-glycinnitrile. 2-(2',3'-Acetyl-5'-tert.-butyldiphenylsilyl-β-D-ribofuranosyl)-N-Cbz-D,L-glycinnitrile (1.52 g, 2.36 mmol) was dissolved in dioxane (15 mL) and Pd—C (10%, 0.3 g) was added. The solution was stirred at AT for 8 h under H$_2$-atmosphere. Pd—C was filtered off and the solvent removed by evaporation followed by coevaporation with EtOAc. Chromatography (silica gel (200 g), EtOAc/hexane 1:2) yielded 2-(2',3'-acetyl-5-tert.-butyldiphenylsilyl-β-D-ribofuranosyl)-D,L-glycinnitrile (877 mg, 73%) as a light yellow oil. MS m/z (rel intensity) 512 (M$^+$+2; 18), 511 (M$^+$+1; 49), 199 (61), 137 (50), 135 (100); IR (CHCl$_3$): 3410, 3330, 2960, 2930, 2890, 2860, 1750 (br.), 1470, 1430, 1370, 1250, 115, 1090, 1020, 980; $^1$H-NMR (CDCl$_3$): 1.06 (s, 9H, tBu), 1.78 (d, J=7.32, 2H, NH$_2$), 2.07 (s, 3H, Ac), 2.09 (s, 3H, Ac), 3.74 (dd, J=3.0, 11.7, 1H, Ha-C(5')), 3.97 (dd, J=2.7, 11.7, 2H, Hb-C(5')) overlayed with methine H), 4.09–4.13 (m, 1H, H—C(1') or H—C(4')), 4.20–4.23 (m, 1H, H—C(1') or H—C(4)), 5.34–5.43 (m, 2H, H—C(2') and H—C(3')), 7.37–7.47 and 7.64–7.70 (m, 10H, arom. H); (CDCl$_3$, D$_2$O exchange): 1.07 (s, 9H, tBu), 2.07 (s, 3H, Ac), 2.09 (s, 3H, Ac), 3.75 (dd, J=3.0, 11.6, 1H, Ha-C(5')), 3.93 (d, J=2.6, 1H, methine H) 3.97 (dd, J=2.8, 11.6, 2H, Hb-C(5')), 4.104.14 (m, 1H, H—C(1') or H—C(4')), 4.20–4.23 (m, 1H, H—C(1') or H—C(4')), 5.34–5.42 (m, 2H, H—C(2') and H—C(3')), 7.37–7.46 and 7.65–7.71 (m, 10H, arom. H); $^{13}$C-NMR (CDCl$_3$): 19.23 (s, tBu), 20.52 with sh. (q, 2×Ac), 26.84 (q, tBu), 44.54 (d, methine C), 63.57 (t, C(5')), 70.89, 71.89, 82.25 and 82.61 (d, C(1'), C(2'), C(3') and C(4')), 119.96 (s, CN), 127.89 (double intensity), 129.89, 129.97, 135.47 and 135.70 (d, arom. C(2'), arom. C(3') and arom. C(4')), 132.64 and 133.95 (s, arom. C(1')), 169.62 and 170.03 (s, Ac).

2-Amino-3-(2',3'-acetyl-5'-tert.-butyldiphenylsilyl-β-D-ribofuranosyl)-5-methylpyrazine-1-oxide. 2-(2',3'-Acetyl-5'-tert.-butyldiphenylsilyl-β-D-ribofuranosyl)D,L-glycinnitrile (788 mg, 1.54 mmol) and anti-methylglyoxal-1-oxime (175 mg, 2.0 mmol) were dissolved in a dry flask in abs. CHCl$_3$ (4.0 mL). The mixture was heated at reflux for 7 days. The solvent was removed by evaporation followed by coevaporation with EtOAC. Chromatography (silica gel (80 g), EtOAc) yielded 2-amino-3-(2',3'-acetyl-5'-tert.-butyldiphenylsilyl-β-D-ribofuranosyl)-5-methylpyrazine-1-oxide (514 mg, 58%) as slightly yellow semicrystalline foam. FAB-MS (3-NOBA): 580 (M$^+$+1); IR (KBr): 3450, 3330, 2960, 2930, 2860, 1745 (br.), 1610, 1560, 1490, 1470, 1430, 1370, 1335, 1250, 1140, 1110, 1090, 1040, 980, 900, 845; UV (EtOH): 255 sh (6880), 345 (7660); $^1$H-NMR (CDCl$_3$): 1.06 (s, 9H, tBu), 2.08 (s, 3H, Ac), 2.09 (s, 3H, Ac), 2.31 (d, J=0.5, 3H, Me—C(3)), 3.86 (dd, J=2.7, 11.6, 1H, Ha-C(5')), 3.93 (dd, J=2.5, 11.6, 1H, Hb-C(5')), 4.20 (ddd, J=2.5, 2.7, 3.7, 1H, H—C(4')), 5.15 (d, J=7.6, 1H, H—C(1')), 5.55 (dd, J=3.7, 5.7, 1H, H—C(3')), 5.78 (dd, J=5.7, 7.6, 1H, H—C(2')), 6.13 (s, br., 2H, NH$_2$), 7.34–7.46, 7.52–7.60 and 7.66–7.68 (m, 10H, arom. H), 7.87 (s, 1H, CH-Py); $^{13}$C-NMR (CDCl$_3$): 19.18 (s, tBu), 20.50, 20.56 and 20.66 (q, Me—C(3) and 2×Ac), 26.89 (q, tBu), 63.47 (t, C(5')), 71.67, 72.11, 81.76 and 84.07 (d, C(1'), C(2'), C(3') and C(4')), 127.87, 127.95, 135.41 and 135.72 (d, arom. C(2') and arom. C(3')), 129.49 (d, C(6)), 129.98 and 130.08 (d, arom. C(4')), 132.24 and 132.58 (s, arom. C(1')), 137.61, 141.48 and 143.71 (s, C(2), C(3) and C(5)), 169.55 and 169.74 (s, 2×Ac).

2-Acetoxy-5-(2',3'-acetyl-5'-tert.-butyldiphenylsilyl-β-D-ribofuranosyl)-6-diacetylamino-3-methylpyrazine. KOAc (104 mg, 1.06 mmol) was suspended in acetic acid anhydride (5.0 mL) and 2-amino-3-(2',3'-acetyl-5'-tert.-butyldiphenylsilyl-β-D-ribofuranosyl)-5-methylpyrazine-1-oxide (560 mg, 0.96 mmol) added. The resulting suspension was heated 15 min. to reflux at 140° C. After cooling to RT the resulting oil was treated with CH$_2$Cl$_2$. KOAc was removed by filtration and the product adsorbed on silica gel (2 g) with evaporation of the solvent. Chromatography (silica gel (30 g), EtOAc/hexane 3:7) yielded 2-acetoxy-5-(2',3'-acetyl-5'-tert.-butyldiphenylsilyl-β-D-ribofuranosyl)-6-diacetylamino-3-methylpyrazine (558 m g, 82%) as a foam. FAB-MS (3-NOBA): 706 (M$^+$+1); IR (CHCl$_3$): 2960, 2930, 2860, 1785 (br.), 1745 (br.), 1730 (br.), 1470, 1430, 1370, 1325, 1170, 1150, 1110, 1090, 1050, 1010, 900 (br.); UV (EtOH): 273 (7800), 285 (5560); $^1$H-NMR (CDCl$_3$): 1.01 (s, 9H, tBu), 2.03 (s, br., 3H, N—Ac-Py), 2.05 (s, 3H, O—Ac), 2.09 (s, 3H, O—Ac), 2.39 (s, 3H, O—Ac-Py or Me—C(3)), 2.40 (s, 3H, O—Ac-Py or Me—C(3)), 2.56 (s, br., 3H, N—Ac-Py), 3.72 (dd, J=3.2, 11.3, 1H, Ha-C(5')), 3.75 (dd, J=3.3, 11.3, 1H, Hb-C(5')), 4.18 (ddd, J=3.2, 3.3, 4.0, 1H, H—C(4')), 4.99 (d, J=6.4, 1H, H—C(1')), 5.69 (dd, J=4.0, 5.4, 1H, H—C(3')), 6.04 (dd, J=5.4, 6.4, 1H, H—C (2')), 7.26–7.42, 7.55–7.57 and 7.60–7.63 (m, 10H, arom. H); $^{13}$C-NMR (CDCl$_3$): 18.92 (q, Me—C(3)), 19.09 (s, tBu), 20.57, 20.76 and 20.84 (q, 3×O—Ac), 26.73 (q, tBu), 26.31 and 27.00 (q, 2×N—Ac), 63.41 (t, C(5')), 72.21, 73.25, 77.78 and 83.80 (d, C(1'), C(2'), C(3') and C(4')), 127.63, 127.73, 135.58 and 135.69 (d, arom. C(2') and arom. C(3')), 129.71 and 129.81 (d, arom. C(4')), 132.78 and 132.93 (s, arom. C(1')), 143.87, 147.68, 148.34 and 151.85 (s, C(2), C(3), C(5) and C(6)), 167.91, 169.45 and 169.81 (s, 3×O—Ac), 171.91 and 172.93 (s, 2×N—Ac).

5-(2',3'-Acetyl-β-D-ribofuranosyl)-6-diacetylamino-3-methylpyrazin-2 one. 2-Acetoxy-5-(2',3'-acetyl-5'-tert.-butyldiphenylsilyl-β-D-ribofuranosyl)-6-diacetylamino-3-methylpyrazine (100 mg, 0.14 mmol), TBAF (67 mg, 0.21 mmol) and HOAc (16 μL, 0.28 mmol) were dissolved in abs. THF (1 mL) and stirred at RT for 23 h. The solvent was evaporated, the resulting oil dissolved in CH$_2$Cl$_2$ and extracted with H$_2$O. The organic layer was dried (MgSO$_4$) and the solvent evaporated. Chromatography (silica gel (8.5 g), CH$_2$Cl$_2$/EtOH 10:1) yielded 5-(2',3'-acetyl-β-D-ribofuranosyl)-6-diacetylamino-3-methylpyrazin-2-one (63 mg, 60%) as slightly yellow oil. FAB-MS (3-NOBA): 426 (M$^+$+1); IR (CHCl$_3$): 3290 (br.), 2930, 2870, 1745 (br.), 1725 (sh), 1660, 1625, 1545, 1460, 1430, 1370, 1110, 1080, 1060, 1035, 1010, 950, 910; $^1$H-NMR (CDCl$_3$): 2.00 (s, 3H, O—Ac), 2.13 (s, 3H, O—Ac), 2.29 (s, br., 3H, N—Ac-Py), 2.42 (s, br., 3H, N—Ac-Py), 2.52 (s, 3H, Me—C(3)), 3.73 (dd, J=1.7, 12.6, 1H, Ha-C(5')), 3.90 (dd, J=2.5, 12.6, 1H, Hb-C(5')), 4.25–4.27 (m, 1H, H—C(4')), 4.87 (d, J=6.7, 1H, H—C(1')), 5.54 (dd, J=2.7, 5.3, 1H, H—C(3')), 5.62 (dd, J=5.3, 6.7, 1H, H—C(2')); $^{13}$C-NMR (CDCl$_3$): 19.58, 20.46 and 20.81 (q, Me—C(3) and 2×O—Ac), 26.03 and 26.36 (q, 2×N—Ac), 62.93 (t, C(5')), 73.58, 75.29, 76.82 and 85.17 (d, C(1'), C(2'), C(3') and C(4')), 136.80 (double intensity), 152.02 and 158.15 (s, C(2), C(3), C(5) and C(6)), 169.40 and 170.04 (s, 2×O—Ac), 171.66 and 172.31 (s, 2×N—Ac).

6-Amino-3-methyl-5-(β-D-ribofuranosyl)-pyrazin-2-one 5'-triphosphate. 5-(2',3'-Acetyl-β-D-ribofuranosyl)-6-diacetylamino-3-methylpyrazin-2-one (24 mg, 56 μmol) was dried by repeated evaporation from abs. pyridine followed by placing 1 h over P$_2$O$_5$ under high vacuum. Pyridine (abs., 56 μL) and abs. dioxane (abs., 166 μL) were added under an Ar atmosphere. To the yellow solution was added a solution of 2-chloro-4H-1,3,2-benzodioxaphosphorin-4-one (67.8 μL, 62 mmol), prepared from reagent (188 mg) in abs. dioxane. After being stirred for 10 min at RT, a solution of triethylammonium pyrophosphate (32 mg, 56 μmol) and tri-N-butylamine (56.4 μL, 237 μmol) in abs. DMF (171 μL) was injected. The mixture was stirred for 10 min. at RT, and then diluted with a solution of iodine (1%) in pyridine/H$_2$O 98:2 (1.12 mL). After 15 min, the excess iodine was quenched by addition of a solution of aqueous sodium pyrosulfite (5%). The solvent was removed by evaporation and the product dried 2 h under high vacuum. The product was dissolved in H$_2$O (1 mL) and the solution allowed to stand for 30 min. at RT. The solvent was removed by evaporation and the residue dissolved in hydrazine hydrate (Fluka,×H$_2$O, 0.5 mL) and stirred for 2 h at RT. Chromatography (DEAE Sephadex-A25; column 19×3 cm; eluent A: 400 mL 0.1 M TEAB pH 7.0, eluent B: 400 mL 1.0 M TEAB pH 7.0; linear gradient 0–100% B; flow 3–4 mL/min: detection by UV-absorption at 254 and 360 nm) followed by lyophilisation yielded 6-amino-3-methyl-5-(β-D-ribofuranosyl)-pyrazin-2-one 5'-triphosphate (15 mg) as a slightly yellow solid. For further purification, reversed phase HPLC was performed (column: Supelco LC-18-DB, 25 cm×10 mm, particle size 5 μm; eluent A: 0.1 M TEAB pH 7.0, eluent B: CH$_3$CN; linear gradient 0–4% B in 30 min.; flow 4.0 mL/min. detection by UV-Absorption at 254 nm: t$_R$ 23 min.). Fractions containing product were pooled and the solvent removed by evaporation to yield 6-amino-3-methyl-5-(β-D-ribofuranosyl)-pyrazin-2-one 5'-triphosphate (3 mg) as a white solid. Negative FAB-MS (glycerin): 496 (monoanion); $^1$H-NMR (D$_2$O): 2.16 (s, 3H, Me—C(3)), 4.13–4.20 (m, 2H, H—C(4') and Ha-C(5')), 4.27 (ddd, J=3.5, 12.0, J$_{H-P}$=6.4, 1H, Hb-C(5')), 4.40 (dd, J=3.0, 6.2, 1H, H—C(3')), 4.43 (dd, J=6.2, 8.3, 1H, H—C(2')), 4.70 (d, J=8.3, 1H, H—C(1')); $^1$H-NMR (31P-decoupled, D$_2$O): 2.16 (s, 3H, Me—C(3)), 4.134.20 (m, 2H, H—C(4') and Ha-C(5')), 4.27 (dd, J=3.5, 12.0, 1H, Hb-C(5')), 4.40 (dd, J=3.0, 6:2, 1H, H—C(3')), 4.44 (dd, J=6.2, 8.3, 1H, H—C(2')), 4.69 (d, J=8.3, 1H, H—C(1')); $^{31}$P-NMR (D$_2$O): –21.62 (t, J=19.3, 20.5, βP), –10.69 (d, J=19.3, αP), –5.56 (d, J=20.5, γP).

2-[2'-Benzoyl-3',5'-O-(tetraisopropyldisiloxane-1,3-diyl)-(β-D-ribofuranosyl]-N-Cbz-D,L-glycinnitrile. Crude 2-(β-D-ribofuranosyl)-N-Cbz-D,L-glycinnitrile (9.58 g, impure, ≦25.8 mmol) and imidazole (7.0 g, 103.2 mmol) were dissolved in abs. DMF (96 mL) and the resulting solution cooled to 0° C. Over a period of 30 min, TIBSCl (8.1 mL, 25.8 mmol) was slowly added at 0° C. After being stirred for 1 h, the solution was poured on H$_2$O (400 mL) and extracted with CH$_2$Cl$_2$. The organic layer was extracted sequentially with sat. aq. NH$_4$Cl, sat. aq. NaHCO$_3$, H$_2$O and sat. aq. NaCl soln., dried (MgSO$_4$) and the solvent removed by distillation to yield crude intermediate (16.80 g). This compound (7.0 g, 12.4 mmol, crude material) was dried by repeated evaporation from toluene and placing over night under high vaccum. Abs. pyridine (30 mL) was added and the resulting solution cooled to 0° C. Benzoyl chloride (1.73 mL, 14.9 mmol) was added slowly, and the solution was warmed to RT and stirred for 3 h at RT. The solution was then cooled in ice/H$_2$O, methanol (7 mL) was added. and the solution poured on H$_2$O. After extraction with CH$_2$Cl$_2$ and washing with sat. aq. NaHCO$_3$, sat. aq. NH$_4$Cl, H$_2$O and sat. aq. NaCl solns. the organic layer was dried (MgSO$_4$) and the solvent evaporated to yield 2-[2'-benzoyl-3',5'-O-(tetraisopropyldisiloxane-1,3-diyl)-β-D-ribofuranosyl]-N-Cbz-D,L-glycinnitrile (8.0 g, 95%). An analytical sample of the diastereomer mixture was obtained by chromatography (silica gel, EtOAc/petroleum ether 3:1). a: major diastereomer, b: minor diastereomer. FAB-MS (3-NOBA): 669 (M$^+$+1); $^1$H-NMR (CDCl$_3$): 0.84–1.11 (m, 2×28H, iProp), 3.93–3.96 (m, 2×1H, H—C(4'a) and H—C(4'b)), 4.01 (dd, J=2.6, 13.1, 1H, Ha-C(5'a)), 4.04 (dd, J=3.0, 12.9, 1H, Ha-C(5'b)), 4.08 (dd, J=3.8, 12.9, 1H, Hb-C(5'b)), 4.13 (dd, J=2.4 13.1, 1H, Hb-C(5'a)), 4.23 (d, J=2.7, 3.7, 1H, H—C(1'b)), 4.30 (s, very br., 1H, H—C(1'a)), 4.40–4.44 (tripletoide m, br., 1H, H—C(3'a)), 4.58 (dd, J=6.2, 8.6, 1H, H—C(3'b)), 5.05–5.11 (m, 2×1H, methine H), 5.13–5.19 (m, 2×2H, methylen H), 5.23 (dd, J=1.9, 6.1, 1H, H—C(2'a)), 5.35–5.38 (m, 1H, H—C(2'b)), 5.64 (d, br., J=9.1, 1H, NHb), 5.90 (d, br., J=9.4, 1H, NHa), 7.31–7.38 (m, 2×5H, arom.-H-Bn), 7.43–7.47 (m, 2×2H, arom.-meta-H-Bz), 7.58–7.61 (m, 2×1H, arom.-para-H-Bz), 8.04–8.07 (m, 2×2H, arom.-ortho-H-Bz); $^{13}$C-NMR (CDCl$_3$): 12.65, 12.68, 12.76, 12.86, 12.96, 13.06, 13.21 and 13.23 (d, isoprop), 16.83, 16.85, 18.86, 16.95, 16.96, 17.02, 17.21, 17.29, 17.33 and 17.48 (q, isoprop), 44.86 (d, methine Ca), 45.77 (d, methine Cb), 60.00 (t, C(5'a)), 60.93 (t, C(5'b)), 67.89 (t, methylen Cb), 68.04 (t, methylen Ca), 69.98, 74.14, 81.87 and 82.56 (d, C(1'a), C(2'a), C(3'a) and C(4'a)), 70.74, 73.76, 81.73 and 82.00 (d, C(1'b), C(2'b), C(3'b) and C(4'b)), 116.02 (s, CNb), 116.80 (s, CNa), 128.28, 128.48, 128.52, 128.61, 126.63, 129.34, 129.80, 129.84, 133.43 and 133.58 (d, aromat. CH), 134.54 and 135.48 (s, arom. C(1'a) and arom. C(1'b)), 154.99 (s, carbamate Cb), 155.40 (s, carbamate Ca), 165.81 (s, Bzb), 166.29 (s, Bza).

2-[2'-Benzoyl-3',5'-O-(tetraisopropyldisiloxane-1,3-diyl)-β-D-ribofuranosyl]-D,L-glycinnitrile. Pd—C (200 mg) was suspended under Ar atmosphere in MeOH (5 mL) and a solution of 2-[2'-benzoyl-3',5'-O-(tetraisopropyldisiloxane-1,3-diyl)-β-D-ribofuranosyl]-N-Cbz-D,L-glycinnitrile (4.0 g, 5.9 mmol) in a mixture of THF (5 mL) and MeOH (35 mL) was added. The suspension was stirred under an H$_2$ atmosphere over night. The catalyst was removed by filtration on celite and the solvent evaporated. Chromatography (silica gel, EtOAc/Petroleum ether 8:2 then 7:3 then 1:1) of the crude material (3.2 g) resulted in separation of the two diastereoisomers of 2-[2'-benzoyl-3',5'-O-(tetraisopropyldisiloxane-1,3-diyl)-β-D-ribofuranosyl]-N-Cbz-D,L-glycinnitrile. The major diastereomer eluted first (1.23 g, 39%), the minor diastereomer later (0.61 g, 19%). An analytical sample of the major diastereomer was obtained by recrystallisation from pentane. Experiments with higher H$_2$ pressure (10 bar) and reduced reaction time (4 h) did not result in improved yields. Major diastereomer m.p. 111–112° C.; FAB-MS (3-NOBA): 535 (M$^+$+1); $^1$H-NMR (CDCl$_3$): 0.86–1.11 (m, 28H, isoprop), 1.87 (d, br., J=8.6, 2H, NH$_2$), 3.97 (ddd, J=2.4, 2.4, 9.1 Hz, 1H, H—C (4')), 4.01 (dd, J=2.7, 13.0, 1H, Ha-C(5')), 4.04–4.07 (m, 1H, methine H), 4.16 (dd, J=2.2, 13.0, 1H, Hb-C(5')), 4.29–4.30 (m, 1H, H—C(1')), 4.54 (dd, J=5.9, 9.1, 1H, H—C(3')), 5.41 (dd, J=1.7, 5.9, 1H, H—C(2')), 7.44–7.47 (triplettoide m, 2H, arom. H—C(3')), 7.57–7.60 (triplettoide m, 1H, arom. H—C(4')), 8.05 (dd, J=1.3, 8.4, 2H, arom. H—C(2')); $^{13}$C-NMR (CDCl$_3$): 12.69, 12.70, 13.02, 13.10 and 13.33 (d, isoprop), 16.87, 16.91, 16.93, 17.02, 17.28, 17.33, 17.37 and 17.47 (q, isoprop), 44.96 (d, methine C), 60.22 (t, C(5')), 69.86, 74.68, 81.96 and 83.57 (d, C(1'), C(2'), C(3') and C(4')), 120.23 (s, CN), 128.46 and 129.74 (d, arom. C(2') and arom. C(3')), 129.81 (s, arom. C(1')), 133.30 (d, arom. C(4')), 166.17(s, Bz). Anal. calc. for $C_{26}H_{42}N_2O_6Si_2$ (534.80): C, 58.39, H, 7.92, N, 5.24; found: C, 58.24, H, 7.87, N, 5.25. Minor diastereomer. FAB-MS (3-NOBA): 535 ($M^+$+1); $^1$H-NMR (CDCl$_3$): 0.81–1.12 (m, 28H, isoprop), 1.92 (s, br., 2H, NH$_2$), 3.96 (ddd, J=3.1, 3.4, 8.7 Hz, 1H, H—C(4')), 4.05 (dd, J=2.9, 12.8, 1H, Ha-C(5')), 4.094.13 (m, 2H, methine H and Hb-C(5')), 4.22 (dd, J=2.5, 6.3, 1H, H—C(1')), 4.55 (dd, J=6.1, 8.7, 1H, H—C(3')), 5.41 (dd, J=2.4, 6.1, 1H, H—C(2')), 7.43–7.47 (triplettoide m, 2H, arom. H—C(3')), 7.56–7.60 (triplettoide m, 1H, arom. H—C(4')), 8.05–8.07 (dupplettoide m, 2H, arom. H—C(2')); $^{13}$C-NMR (CDCl$_3$): 12.68, 12.72, 13.05, and 13.25 (d, isoprop), 16.84, 16.86, 16.96, 17.03, 17.29, 17.34 and 17.47 (q, isoprop), 46.29 (d, methine C), 60.94 (t, C(5')), 70.68, 74.15, 81.80 and 83.40 (d, C(1'), C(2'), C(3') and C(4')), 119.14 (s, CN), 128.43 and 129.74 (d, arom. C(2') and arom. C(3')), 129.71 (s, arom. C(1')), 133.28 (d, arom. C(4')), 165.83 (s, Bz).

2-Amino-3-[2'-benzoyl-3',5'-O-(tetraisopropyldisiloxane-1,3-diyl)-β-D-ribofuranosyl]-5-methylpyrazine-1-oxide. Dry 2-[2'-benzoyl-3',5'-O-(tetraisopropyldisiloxane-1,3-diyl)-β-D-ribofuranosyl]-D,L-glycinnitrile (major diastereomer, 1.12 g, 2.09 mmol), methylglyoxal-1-oxime (235 mg, 2.7 mmol) and pyridine hydrochloride (23 mg, 0.2 mmol) were dissolved in abs. CHCl$_3$ and heated to reflux over night. The solvent was evaporated. Chromatography (silica gel (150 g), EtOAc/petroleum ether 3:7 then 1:1 then 7:3) of the dark brown oil (1.58 g) yielded 2-amino-3-[2'-benzoyl-3',5'-O-tetraisopropyldisiloxane-1,3-diyl)-β-D-ribofuranosyl]-5-methylpyrazine-1-oxide (676 mg, 54%) as a foam. Reaction of the minor diastereomer yielded the same product. FAB-MS (3-NOBA): 604 ($M^+$+1); $^1$H-NMR (CDCl$_3$): 0.83–1.13 (m, 28H, isoprop), 2.35 (d, J=0.5 Hz, 3H, Me—C(5)), 4.02–4.18 (m, 3H, H—C(4'), Ha-C(5') and Hb-C(5')), 4.60 (dd, J=5.2, 8.9, 1H, H—C(3')), 5.31 (d, J=1.3, 1H, H—C(1')), 5.94 (dd, J=1.3, 5.2 Hz, 1H, H—C(2')), 6.13 (s, br., 2H, NH$_2$), 7.44–7.48 (triplettoide m, 2H, arom. H—C(2')), 7.57–7.61 (triplettoide m, 1H, arom. H—C(4')), 7.88 (s, 1H, H—C(6)), 8.09–8.11 (dupplettoide m, 2H, arom. H—C(3')); $^{13}$C-NMR (CDCl$_3$): 12.64, 12.92, 13.04 and 13.29 (d, isoprop), 16.77, 16.80, 16.86, 16.92, 17.18, 17.30, 17.34 and 17.51 (q, isoprop), 20.52 (q, Me—C(5)), 60.36 (t, C(5')), 70.58, 76.48, 81.93 and 83.51 (d, C(1'), C(2'), C(3') and C(4')), 128.38 and 129.77 (d, arom. C(2')), and arom. C(3')), 129.21 (d, C(6)), 130.02 (s, arom. C(1')), 133.14 (d, arom. C(4')), 138.84, 141.78 and 143.65 (s, C(2), C(3) and C(5)), 165.73 (s, Bz). Anal. calc. for $C_{29}H_{45}N_3O_7Si_2$ (603.86): C, 57.68, H, 7.51, N, 6.96; found: C, 57.88, H, 7.51, N, 6.93.

2-Acetoxy-5-[2'-benzoyl-3',5'-O-(tetraisopropyldisiloxane-1,3-diyl)-β-D-ribofuranosyl]-6-diacetylamino-3-methylpyrazine. 2-Amino-3-[2'-benzoyl-3',5'-O-tetraisopropyldisiloxane-1,3-diyl)-β-D-ribofuranosyl]-5-methylpyrazine-1-oxide (676 mg, 1.12 mmol) and KOAc (275 mg, 2.8 mmol) were suspended in Ac$_2$O (8 mL) and heated at reflux for 20 min. The reaction mixture was cooled to RT, the solvent evaporated under high vacuum and the dark brown residue suspended in CH$_2$Cl$_2$. KOAc was removed by filtration. Chromatography (silica gel (80 g), petroleum ether/EtOAc 8:2) yielded 2-acetoxy-5-[2'-benzoyl-3',5'-O-(tetraisopropyldisiloxane-1,3-diyl)-β-D-ribofuranosyl]-6-diacetylamino-3-methylpyrazine (490 mg, 60%) as a foam. FAB-MS (3-NOBA): 730 ($M^+$+1); $^1$H-NMR (CDCl$_3$): 0.82–1.14 (m, 28H, isoprop), 2.07 (s, br., 3H, N—Ac), 2.38 and 2.52 (s, 2×3H, Me—C(3) and O—Ac), 2.54 (s, br., 3H, N—Ac), 3.94 (dd, J=2.7, 12.9, 1H, Ha-C(5')), 4.01 (dd, J=2.8, 12.9, 1H, Hb-C(5')), 4.07 (ddd, J=2.7, 2.7, 9.1, 1H, H—C(4')), 4.74 (dd, J=4.9, 9.1, 1H, H—C(3')), 5.06 (d, J=1.1, 1H, H—C(1')), 4.92 (d, br., J=4.9, 1H, H—C(2')), 7.43–7.47 (triplettoide m, 2H, arom. H—C(2')), 7.55–7.59 (triplettoide m, 1H, arom. H—C(4')), 8.06–8.09 (duplettoide m, 2H, arom. H—C(3')); $^{13}$C-NMR (CDCl$_3$): 12.52, 12.72, 13.04 and 13.34 (d, isoprop), 16.79, 16.84, 17.03, 17.10, 17.23, 17.27, 17.30 and 17.38 (q, isoprop), 18.92 and 20.85 (q, Me—C(3) and O—Ac), 26.30 and 26.99 (q, 2×N—Ac), 60.55 (t, C(5')), 70.81, 75.87, 79.58 and 81.99 (d, C(1'), C(2'), C(3') and C(4)), 128.33 and 129.76 (d, arom. C(2') and arom. C(3')), 130.20 (s, arom. C(1')), 132.97 (d, arom. C(4')), 143.27, 147.82, 148.96 and 151.57 (s, C(2), C(3), C(5) and C(6)), 165.46 and 167.92 (s, O-Bz and O—Ac), 172.16 and 172.93 (s, 2×N—Ac). Anal. calc. for $C_{35}H_{51}N_3O_{10}Si_2$ (729.98): C, 57.59, H, 7.04, N, 5.76; found: C, 57.87, H, 7.24, N, 5.82.

6-Acetylamino-5-[2'benzoyl-3',5'-O-(tetraisopropyldisiloxane-1,3-diyl)-β-D-ribofuranosyl]-3-methylpyrazin-2-one. 2-Acetoxy-5-[2'-benzoyl-3',5'-O-tetraisopropyldisiloxane-1,3 diyl)-β-D-ribofuranosyl]6-diacetylamino-3-methylpyrazine (458 mg, 0.63 mmol) was dissolved in abs. EtOH (46 mL) and heated at reflux for 28 h. The solvent was evaporated and crude 6-acetylamino-5-[2'-benzoyl-3',5'-O-(tetraisopropyldisiloxane-1,3 diyl)-β-D-ribofuranosyl]-3-methylpyrazin-2-one (433 mg) was isolated as an oil, which was used for the next reaction without further purification. Chromatography (silica gel, petroleum ether/EtOAc 2:3) yielded an analytical sample. FAB-MS (3-NOBA): 645 ($M^+$; $^1$H-NMR (CDCl$_3$): 0.83–1.13 (m, 28H, isoprop), 2.21 and 2.36 (s, 2×3H, N—Ac and Me—C(3)), 4.06 (dd, J=2.4, 13.3, 1H, Ha-C(5')), 4.14–4.17 (m, 1H, H—C(4')), 4.21 (d, br., J=13.4, 1H, Hb-C(5')), 4.49 (dd, J=4.7, 9.3, 1H, H—C(3')), 5.30 (d, J=0.8, 1H, H—C(1')), 5.83 (d, br., J=4.7, 1H, H—C(2')), 7.45–7.49 (triplettoide m, 2H, arom. H—C(2')), 7.52–7.61 (triplettoide m, 1H, arom. H—C(4')), 8.08–8.11 (duplettoide m, 2H, arom. H—C(3')), 9.95 and 12.28 (s, br., 2×1H, 2×NH); $^{13}$C-NMR (CDCl$_3$): 12.48, 12.66, 12.97 and 13.50 (d, isoprop), 16.82, 16.86, 16.90, 16.91, 16.96, 17.03, 17.19 and 17.30 (q, isoprop), 19.94 and 24.69 (q, Me—C(3) and N—Ac), 59.71 (t, C(5')), 68.93, 77.82, 81.85 and 83.94 (d, C(1'), C(2'), C(3') and C(4')), 128.40 and 129.72 (d, arom. C(2') and arom. C(3')), 130.07 (s, arom. C(1')), 133.14 (d, arom. C(4')), 112.83, 133.46, 150.97 and 153.74 (s, C(2), C(3), C(5) and C(6)), 165.53 (s, O-Bz), 171.54 (s, N—Ac).

6-Acetylamino-5-[2'-benzoyl-3',5'-O-(tetraisopropyldisiloxane-1,3-diyl)-β-D-ribofuranosyl]-2-benzyloxy-3-methylpyrazine. Dry 6-acetylamino-5-[2'-benzoyl-3',5'-O-(tetraisopropyldisiloxane-1,3-diyl)-β-D-ribofuranosyl]-3-methylpyrazine-2-one (323 mg, 0.50 mmol), triphenylphosphine (197 mg, 0.75 mmol) and benzylalcohol (124 μL, 0.60 mmol) were dissolved in abs. THF (6 mL) and cooled to 0° C. DEAD (118 μL, 0.75 mmol) was added over a period of 5 min. The solution was warmed to RT, stirred for 30 min. and the solvent evaporated. The crude product was adsorbed to silica gel. Chromatography (silica gel, petroleum ether/EtOAc 8:2) yielded 6-acetylamino-5-[2'-benzoyl-3',5'-O-(tetraisopropyldisiloxane-1,3-diyl)-β-D-ribofuranosyl]-2-benzyloxy-3-methylpyrazine (206 mg, 56%) as an amorphous solid. FAB-MS (3-NOBA): 736 (M$^+$+1); $^1$H-NMR (CDCl$_3$): 0.90–1.12 (m, 28H, isoprop), 2.24 and 2.43 (s, br., 2×3H, N—Ac and Me—C(3)), 4.00 (dd, J=2.9, 12.7, 1H, Ha-C(5')), 4.06 (dd, J=3.4, 12.7, 1H, Hb-C(5')), 4.11–4.15 (m, 1H, H—C(4')), 4.74 (dd, J=5.0, 8.8, 1H, H—C(3')), 5.24 (d, J=1.2, 1H, H—C(1')), 5.37 (d, J=12.7, 1H, Ha-CH$_2$), 5.40 (d, J=12.7, 1H, Hb-CH$_2$), 6.08 (d, br., J=4.8, 1H, H—C(2')), 7.30–7.48 (m, 7H, Bn arom. H and Bz arom. H—C(3')), 7.56–7.60 (triplettoide m, 1H, Bz arom. H—C(4')), 8.09–8.12 (duplettoide m, 2H, Bz arom. H—C(2')), 8.15 (s, br., 1H, NH); $^{13}$C-NMR (CDCl$_3$): 12.53, 12.72, 13.06 and 13.28 (d, isoprop), 16.83, 16.87, 17.01, 17.11, 17.18, 17.22, 17.27 and 17.37 (q, isoprop), 18.58 and 23.94 (q, Me—C(3) and N—Ac), 61.19 (t, C(5')), 68.23 (t, CH$_2$-Bn), 70.94, 77.20, 80.32 and 81.81 (d, C(1'), C(2'), C(3') and C(4')), 127.59, 128.00, 128.34, 128.51 and 129.75 (d, arom. CH), 130.17 (s, Bz arom. C(1'')), 133.04 (d, Bz arom. C(4'')), 133.48, 139.40 and 140.65 (s, C(2), C(3), C(5), C(6)), 136.48 (s, Bn arom. C(1'')), 156.05 and 166.07 (s, O-Bz and N—Ac). Anal. calc. for C$_{38}$H$_{53}$N$_3$O$_8$Si$_2$ (735.9): C, 62.01, H, 7.26, N, 5.71; found: C, 62.17, H, 7.38, N, 5.80.

6-Acetylamino-5-(O-2'-benzoyl-β-D-ribofuranosyl)-2-benzyloxy-3-methylpyrazine. 6-Acetylamino-5-[2'-benzoyl-3',5'-O-(tetraisopropyldisiloxane-1,3-diyl)-β-D-ribofuranosyl]-2-benzyloxy-3-methylpyrazine (100 mg, 136 μmol) was dissolved in a precooled (0° C.) solution of pyridine/HF (200 μL, 6%), and the mixture was stirred over night at 0° C. The deprotected product partially precipitated as a white solid. MeOSiMe$_3$ (230 μL) was added at 0° C. The solvent was removed by evaporation at <0° C. to yield 6-Acetylamino-5-(O-2'-benzoyl-β-D-ribofuranosyl)-2-benzyloxy-3-methylpyrazine (69 mg, quant.) as a slightly impure white solid. Attempts to further purify the product (chromatography on silica gel; recrystallization) failed due to partial acylmirgration from O-(C2') to O-(C3'). FAB-MS (3-NOBA): 494 (M$^+$+1); $^1$H-NMR (DMSO): 2.05 and 2.41 (s, br., 2×3H, N—Ac and Me—C(3)), 3.48–3.54 (m, 1H, Ha-C(5')), 3.65–3.70 (m, 1H, Hb-C(5')), 3.92–3.96 (m, 1H, H—C(4')), 4.41–4.37 (m, 1H, H—C(3')), 4.89 (dd, J=4.6, 6.5, 1H, OH), 5.24 (d, J=4.1, 1H, H—C(1')), 5.36 (s, 2H, CH$_2$), 5.41 (d, J=6.0, 1H, OH), 5.54 (dd, J=4.2, 5.3, 1H, H—C(2')), 7.32–7.56 (m, 7H, Bn arom. H and Bz arom. H—C(3')), 7.64–7.69 (triplettoide m, 1H, Bz arom. H—C(4')), 8.00–8.03 (duplettoide m, 2H, Bz arom. H—C(2')), 10.01 (s, br., 1H, NH); $^{13}$C-NMR (DMSO): 18.46 and 23.02 (q, Me—C(3) and N—Ac), 61.51 (t, C(5')), 67.56 (t, CH$_2$-Bn), 69.73, 77.00, 78.15 and 84.22 (d, C(1'), C(2'), C(3') and C(4')), 127.77, 127.87, 128.34, 128.50 and 129.32 (d, arom. CH), 129.76 (s, Bz arom. C(1'')), 133.17 (d, Bz arom. C(4'')), 136.39 (s, Bn arom. C(1'')), 137.36, 139.84, 140.31 and 149.51 (s, C(2), C(3), C(5) and C(6)), 155.70 and 164.88 (s, O-Bz and N—Ac).

6-Acetylamino-2-benzyloxy-5-[2'-benzoyl-3',5'-(bis-dibenzylphosphoryl)-β-D-ribofuranosyl]-3-methylpyrazine. 6-Acetylamino-5-(O-2'-benzoyl-β-D-ribofuranosyl)-2-benzyloxy-3-methylpyrazine (68 mg, 136 μmol, raw material from the above reaction), tetrazole (39 mg, 552 μmol) and 3 Å molecular sieves were dried over night under high vacuum above P$_2$O$_5$ and then dissolved in a mixture of abs. DMF (2.1 mL) and abs. Me—CN (1.5 mL). 250 μl of a solution of N,N-diisopropylaminodibenzyloxyphosphine (275 mg, 797 μmol) in abs. Me—CN (1.0 mL) was added at RT. The mixture was stirred for 1 h at RT. 4-Methylmorpholine-4-oxide monohydrate (187 mg, 1.38 mmol) was then added, and the resulting mixture was again stirred at RT for 5.5 h and then filtered through a bed of celite. The solvent was evaported under hiah vacuum and the crude product adsorbed on silica gel (500 mg). Chromatography (silica gel (25 g), EtOAc/petroleum ether 1:1 then 3:1) yielded 6-acetylamino-2-benzyloxy-5-[2'-benzoyl-3',5'-O-(bis-dibenzylphosphoryl)-β-D-ribofuranosyl]-3-methylpyrazine (95 mg, 70%) as a foam. FAB-MS (3-NOBA): 1014 (M$^+$+1); $^1$H-NMR (CDCl$_3$): 2.24 and 2.30 (s, 2×3H, N—Ac and Me—C(3)), 4.16–4.22 (m, 1H, Ha-C(5')), 4.26–4.32 (m, 1H, Hb-C(5')), 4.40–4.43 (m, 1H, H—C(4')), 4.82–5.00 (m, 8H, POCH$_2$), 5.11–5.16 (m, 1H, H—C(3')), 5.29 (d, J=4.2, 1H, H—C(1')), 5.30 (d, J=12.6, 1H, Ha-CH$_2$PyO), 5.35 (d, J=12.6, 1H, Hb-CH$_2$PyO), 5.88–5.90 (triplettoide m, 1H, H—C(2')), 7.15–7.43 (m, 22H, arom. H), 7.55–7.60 (triplettoide m, 1H, Bz arom. H—C(4')), 8.03–8.05 (duplettoide m, 2H, Bz arom. H—C(2')), 8.28 (s, br., 1H, NH); $^{13}$C-NMR (CDCl$_3$): 18.71 and 24.01 (q, Me—C(3) and N—Ac), 66.74 (td, J$_{CP}$=5.1, C(5')), 67.56 (t, CH$_2$OPy), 69.27, 69.32, 69.39, 69.44, 69.63, 69.69, 69.75, 69.81 (4×td, 4×CH$_2$OP), 74.49 and 79.94 (d, C(1') and C(2')), 74.52 (dd, J$_{CP}$=5.1, C(3')), 81.03 (tripplettoide m, C(4')), 127.76, 127.80, 127.87, 127.92, 127.96, 128.07, 128.45, 128.48, 128.53, 128.56 and 128.63 (d, arom. CH), 129.26 (s, Bz arom. C(1'')), 129.93 (d, arom. CH), 133.53 (d, Bz arom. C(4'')), 135.30, 135.38, 135.60, 135.67 135.73, 139.75 and 140.98 (s, arom. C), 136.39 (s, PyOBn arom. C(1'')), 156.42 and 165.79 (s, O-Bz and N—Ac); $^{31}$P-NMR (1H-decoupled) (CDCl$_3$): −0.98 (s, PO$_4$), −1.64 (s, PO$_4$); Anal. calc. for C$_{54}$H$_{53}$N$_3$O$_{13}$P$_2$ (1013.9): C, 63.97, H, 5.27, N, 4.14; found: 63.07, H, 5.24, N, 4.05.

6-Amino-3-methyl-5-(β-D-ribofuranosyl)-pyrazin-2-one 3',5'-bisphosphate. 6-Acetylamino-2-benzyloxy-5-[2'-benzoyl-3',5'-O-(bis-dibenzylphosphoryl)-α-D-ribofuranosyl]-3-methylpyrazine (133 mg, 0.131 mmol) was dissolved in THF (2.6 mL) and aq. TEAB (1.3 mL, 0.2 M, pH 7.4) was added. Under Ar atmosphere PdOH—C (ca. 15 mg, 20%) was added and the reaction mixture stirred over night at RT in an H$_2$ atmosphere. The catalyst was filtered off and the solvent removed by evaporation. After drying under high vacuum the resulting yellow oil was dissolved in hydrazine hydrate (1.2 mL). After being stirred for 1 h at RT, the reaction mixture was cooled in N$_2$(1) and the solvent evaporated at low temperature. Ion exchange chromatography (DEAE Sephadex-A25; column 55×1.8 cm; eluent A: H$_2$O (1 L), eluent B: 1.0 M TEAB pH 8.0 (1 L); linear gradient 0–100% B; flow 3–5 mL/min.; fraction size 20–25 mL; detection by UV-absorption at 254 and 360 nm). Fractions containing product 42–46 were pooled and the solvent removed by evaporation. After repeated cycles of dissolution in water followed by lyophilization (to remove the volatile buffer), 6-Amino-3-methyl-5-(β-D-ribofuranosyl)-pyrazin-2-one 3',5'-bisphosphate (25 mg) was obtained as a light brown amorphous solid. FAB-MS negative (glycerin): 416 (monoanion); $^1$H-NMR (D$_2$O): 2.18 (s, 3H, Me—C(3)), 4.03 (ddd, J=11.5, 3.3, 2.3, 1H, Ha-C(5')), 4.11 (ddd, J=11.5, 5.6, 2.4, 1H, Hb-C(5')), 4.36 (s, very br. with sh, 1H, H—C(4')), 4.45 (dd, J=8.9, 5.8, 1H, H—C(2')), 4.63 (ddd, J=7.9, 5.8, 2.3, 1H, H—C(3')), 4.78 (d, J=8.9, 1H, H—C(1')); $^1$H-NMR ($^{31}$P-decoupled) (D$_2$O): 2.16 (s, 3H, Me—C(3)), 4.01 (dd, J=11.5, 2.3, 1H, Ha-C(5')), 4.1 (dd, J=11.5, 2.4, 1H, Hb-C(5')), 4.354.36 (quadruplettoide m, 1H, H—C(4')), 4.44 (dd, J=9.0, 5.7, 1H, H—C(2')), 4.62 (dd, J=5.7, 2.4, 1H, H—C(3')), 4.77 (d, J=9.0, 1H, H—C(1')); $^{13}$C-NMR (D$_2$O): 19.78 (q, Me—C(3)), 67.19 (td, J$_{CP}$=4.6, C(5')) 73.87 (dd, J$_{CP}$=4.9, C(2') or C(3')), 77.12 (dd, J$_{CP}$=4.9, C(2') or C(3')), 85.10 (d, C(1')), 86.49 (ddd, $J_{CP}$=3.2, 8.4, C(4')), 116.30, 140.14, 145.81 and 159.90 (s, C(2), C(3), C(5) and C(6); $^{31}$P-NMR (D$_2$O): 2.14 (d, J=8.0, PO$_4$-(O3')), 1.53 (s, very br., PO$_4$-(O5')); $^{31}$P-NMR $^1$H-decoupled (D$_2$O): 2.14 (s, PO$_4$-(O3')), 1.54 (s, PO$_4$-(O5')).

Synthesis of a protected phosphoramidite of the puDAA deoxyribonucleotides. 8-(β-D-2'-Deoxyribofuranosyl)-4-[(dimethylamino)methyliden]-imidazo[1,2-a]-1,3,5-triazin-2(8H)-one. 8-(β-D-2'-Deoxyribofuranosyl)-4-imidazo[1,2-a]-1,3,5-triazin-2(8H)-one (100 mg, 0.37 mmol, J. J. Voegel, M. M. Altorfer, S. A. Benner, *Helv. Chim. Acta.* 1993, 76, 2061–2069) was suspended in abs. DMF (2.0 mL) and dimethylformamide diethylacetal (0.7 mL) added at r.t. The resulting slightly cloudy soln. was stirred for 6.5 h at RT. The solvents were removed with a Kugelrohr oven at 50° C., the residue coevaporated with toluene, and then dried at high vacuum overnight. Chromatography through silica gel (10 g) (eluant: CH$_2$Cl$_2$/MeOH 9:1 then 8:2) yielded 8-(β-D-2'-deoxyribofuranosyl)-4-[(dimethylamino)methyliden]-imidazo[1,2-a]1,3,5-triazin-2(8H)-one (88 mg, 73%) as a light yellow solid. FAB-MS (3-NOBA): 667 (M$_2^+$+Na; 38), 645 (M$_2^+$+1; 18), 345 (M$^+$+Na; 62), 323 (M$^+$+1; 100); $^1$H-NMR (DMSO): 2.17 (ddd, J=3.1, 6.1, 13.2, 1H, Ha-C (2')), 2.40 (ddd, J=5.8, 7.7, 13.2, 1H, Hb-C(2')), 3.15 (d, J=0.8, 3H, N-Me), 3.24 (d, J=0.5, 3H, N-Me), 3.49–3.59 (m, 2H, H—C(5')), 3.81–3.83 (m, 1H, H—C(4')), 4.30–4.33 (m, 1H, H—C(3')), 5.07 (dd, J=5.5, 5.6, 1H, HO—C(5')), 5.30 (d, J=4.2, 1H, HO—C(3')), 6.16 (dd, J=6.2, 7.6, 1H, H—C (1')), 7.42 (s, 2H, H—C(6) and H—C(7)), 8.819–8.821 (m, 1H, amidine-H); $^1$H-NMR (DMSO, D$_2$O exchange): 2.19 (ddd, J=3.1, 6.2, 13.3, 1H, Ha-C(2')), 2.41 (ddd, J=5.9, 7.6, 13.3, 1H, Hb-C(2')), 3.16 (d, J=0.8, 3H, N-Me), 3.24 (d, J=0.5, 3H, N-Me), 3.51 (dd, J=4.2, 11.8, 1H, Ha-C(5')), 3.57 (dd, J=4.3, 11.8, 1H, Hb-C(5')), 3.82–3.84 (m, 1H, H—C (4')), 4.31–4.34 (m, 1H, H—C(3')), 6.17 (dd, J=6.3, 7.4, 1H, H—C(1')), 7.42 (d, J=2.9, 1H, H—C(7)), 7.44 (dd, J=0.3, 2.9, 1H, H—C(6)), 8.80–8.81 (m, 1H, amidine-H); $^{13}$C-NMR (DMSO): 34.95 (q, N-Me), 38.85 (t, C(2')), 41.04 (q, N-Me), 61.54 (t, C(5')), 70.53 (d, C(3')), 82.78 (d, C(4')), 87.52 (d, C(1')), 107.39 (d, C(6)), 114.96 (d, C(7)), 150.29 (s, C(2)), 153.70 (s, C(8a)), 158.92 (d, CH-amidine), 162.11 (s, C(4)).

8-[2'-Deoxy-5'-O-(4,4'-dimethoxytrityl)-β-D-ribofuranosyl]-4-[(dimethylamino)methyliden]-imidazo[1,2-a]-1,3,5-triazin-2(8H)-one 8-(β-D-2'-Deoxyribofuranosyl)-4-[(dimethylamino)methyliden]-imidazo[1,2-a]-1,3,5-triazin-2(8H)-one (75 mg, 0.23 mmol) was dried over P$_2$O$_5$ under high vacuum for 2 days and then dissolved with warming in abs. DMF (3.5 mL). The soln. was cooled to RT, and a soln. of dimethoxytrityl chloride (103 mg, 0.32 mmol) dissolved in abs. pyridine (0.9 mL) was added. After stirring for 9.5 h at RT, the reaction was quenched with a mixture of MeOH/pyridine 1:1 (0.2 mL), and the solvents removed under high vacuum. Chromatography through silica gel (10 g) (eluant: CH$_2$Cl$_2$/MeOH 100:1 then 100:5 then 100:10, each containing 1% Et$_3$N) yielded 8-[2'-deoxy-5'-O-(4,4'-dimethoxytrityl)-β-D-ribofuranosyl]-4-[(dimethylamino)methyliden]-imidazo[1,2-a]-1,3,5-triazin-2(8H)-one (127 mg, 66%) as a microcrystalline solid with a trace of Et$_3$N as impurity. This was used directly without further purification. FAB-MS (3-NOBA): 625 (M$^+$+1); $^1$H-NMR (CDCl$_3$): 2.43–2.48 (m, 1H, Ha-C(2')), 2.76–2.81 (m, 1H, Hb-C(2')), 3.18 (d, J=0.6, 3H, N-Me), 3.22 (s, 3H, N-Me), –3.28 (dd, J=3.7, 10.5, 1H, Ha-C(5')), 3.42 (dd, J=3.0, 10.5, 1H, Hb-C(5')), 3.78 (s, 6H, O-Me), 4.23–4.24 (m, 1H, H—C (4')), 4.70–4.73 (m, 1H, H—C(3')), 5.45 (s, br., 1H, OH), 6.48 (dd, J=6.2, 6.3, 1H, H—C(1')), 6.80–6.98 (m, 4H, ortho-arom. H), 7.04 (d, J=2.8, 1H, H—C(6) or H—C(7)), 7.10 (d, J=2.8, 1H, H—C(6) or H—C(7)), 7.18–7.44 (m, 9H, arom. H), 8.98 (s, 1H, amidine-H); $^{13}$C-NMR (CDCl$_3$): 34.45 (q, N-Me), 41.46 (t, C(2')), 41.81 (q, N-Me), 55.24 (q, O-Me), 63.67 (t, C(5')), 71.29 (d, C(3')), 83.84 (d, C(1') or C(4')), 86.01 (d, C(1') or C(4')), 86.54 (s, Cq-Trityl), 107.09 (d, C(6)), 113.17 (d, C(2'')), 114.86 (d, C(7)), 126.86 (s, C(4''')), 127.85 and 128.33 (d, C(2''') and C(3''')), 130.20 and 130.21 (d, C(3''a) and C3''b)), 135.69 and 135.80 (d, C(4''a) and C4''b)), 144.61 (s, C(1''')), 150.20 (s, C(2)), 154.65 (s, C(8a)), 158.51 (s, C(1'')), 159.78 (d, CH-amidine), 165.01 (s, C(4)).

8-[2'-Deoxy-5'-O-(4,4'-dimethoxytrityl)-β-D-ribofuranosyl]-4-[(dimethylamino)methylidene]-imidazo[1,2-a]-1,3,5-triazin-2(8H)-one 3'-(2-cyanoethyl)-N,N-diisopropyl-phosphoramidite. 8-[2'-Deoxy-5'-O-(4,4'-dimethoxytrityl)-β-D-ribofuranosyl]-4-[(dimethylamino)methyliden]-imidazo[1,2-a]-1,3,5-triazin-2(8H)-one (125 mg, 0.20 mmol) was dried over P$_2$O$_5$ under high vacuum for 3 days, and then dissolved in abs. CH$_2$Cl$_2$ (1.0 mL). Diisopropylethylamine (137 µL, 0.80 mmol) was added, followed by dropwise addition at RT. of 2-cyanoethyl-N,N-diisopropylchlorophosphoramidite (54 µL, 0.24 mmol). After 1.5 h, Et$_3$N (0.2 mL) was added, the resulting precipitate dissolved in the chromatography elution mixture (1.0 mL) and chromatographed through silica gel (10 g) (eluant: CH$_2$Cl$_2$/MeOH 95:5, containing 1% Et$_3$N) to yield the product 8-[2'-Deoxy-5'-O-(4,4'-dimethoxytrityl)-β-D-ribofuranosyl]-4-[(dimethylamino)methyliden]-imidazo[1,2-a]-1,3,5-triazin-2(8H)-one 3'-(2-cyanoethyl)-N,N-diisopropyl-phosphoramidite (mixture of two diastereomers) as an amorphous white solid (109 mg, 66%). FAB-MS (3-NOBA): 847 (M$^+$+Na), 825 (M$^+$+1); $^1$H-NMR: The numbering of the two diastereomeric phosphoramidites is arbitrary. (CDCl$_3$): 1.16–1.18 (m, 2×12H, Me-isopropyl), 2.42–2.65 (m, 2×4H, H—C(2') and H-(CH$_2$—CN)), 3.166 (s, 3H, N-Me), 3.167 (s, 3H, N-Me), 3.21 (s, 2×3H, N-Me), 3.30–3.34 (m, 2×1H, Ha-C(5')), 3.42 (dd, J=3.2, 10.5, 1H, Hb-C(5'a)), 3.48 (dd, J=3.0, 10.5, 1H, Hb-C(5'b)), 3.53–3.69 and 3.71–3.88 (m, 2×4H, H-(CH-isopropyl) and H-(CH$_2$O-P)), 3.787, 3.792 and 3.793 (s, 2×6H, O-Me), 4.14–4.19 (m, 2×1H, H—C(4')), 4.65–4.71 (m, 2×1H, H—C(3')), 6.45–6.49 (m, 2×1H, H—C(1')), 6.81–6.85 (m, 2×4H, ortho-arom. H), 6.98 (d, J=2.8, 1H, H—C(6a) or H—C(7a)), 7.05 (d, J=2.8, 1H, H—C(6a) or H—C(7a)), 7.08–7.09 (m, 2H, H—C(6b) and H—C(7b)), 7.20–7.34 and 7.41–7.44 (m, 2×9H, arom. H), 8.99 and 9.00 (s, 2×1H, amidine-H); $^{13}$C-NMR (CDCl$_3$): 20.20 (td, J=7.1, CH$_2$a-CN), 20.43 (td, J=7.2, CH$_2$b-CN), 24.47, 24.53, 24.55, 24.57, 24.59, 24.61, 24.63 and 24.64 (q, Me-isopropyl), 35.36 (q, N-Me), 40.05 (t, C(2')), 41.74 (q, N-Me), 43.16, 43.24, 43.26 and 43.34 (d, CH-isopropyl), 55.24 and 55.27 (q, O-Me), 58.18 (td, J=18.7, CH$_2$a-OP), 58.25 (td, J=18.5, CH$_2$b-OP), 63.95 and 63.23 (t, C(5')), 72.80 (dd, J=16.0, C(3a')), 73.60 (dd, J=17.1, C(3b')), 83.34 and 83.40 (d, C(1')), 85.30 (dd, J=6.1, C(4a')), 85.40 (dd, J=3.6, C(4b')), 86.61 and 86.62 (s, Cq-Trityl), 107.43 and 107.45 (d, C(6)), 113.20 (d, C(2'')), 113.98 and 133.99 (d, C(7)), 117.49 and 117.75 (s, CN), 126.99 and 127.03 (s, C(4''')), 127.90, 128.24 and 128.31 (d, C(2''') and C(3''')), 130.15, 130.18 and 130.21 (d, C(3'')), 135.49, 135.52, 135.54 and 135.57 (d, C(4'')), 144.41 and 144.42 (s, C(1''')), 150.59 and 150.67 (s, C(2)), 154.40 and 154.41 (s, C(8a)), 158.62 and 158.63 (s, C(1'')), 159.73 (d, amidine), 164.26 and 164.31 (s, C(4)); $^{31}$P-NMR (CDCl$_3$): 148.8 and 149.0.

EXAMPLE 7

Oligonucleotides

DNA synthesis was performed on an Applied Biosysterns 380B automated oligonucleotide synthesizer. All oligonucleotides were purified by HPLC (Macherey Nagel SS 250 Nucleosil 300-7 C-4; Ec$_3$NH$^+$ acetate (A) and CH$_3$CN (B), 80% (A)/20% (B) to 70% (A)/30% (B) over 20 min, 4 mL/min flow rate), and a sample of each purified template was labeled with P-32 (polynucleotide kinase with [γ-$^{32}$P] ATP) and examined by gel electrophoresis to establish its purity.

Incorporation of non-standard bases into synthetic oligonucleotides was verified by digestion of samples using the procedure of Eritja et. al. (Eritja, R., Horowitz, D. M., Walker, P. A., Ziehler-Martin, J. P., Boosalis, M. S., Goodman, M. F., Itakura, K., & Kaplan, B. E. (1986) *Nucl. Acids Res.* 14, 8135–8153), chromatography of the resulting products, and identification by comparison with authentic standards. Sequences of oligoribonucleotides were determined by the method of Randerath et al. (Randerath, K., Gupta, R. C., & Randerath, E. (1980) *Methods Enzymol.* 65, 638–680).

Nearest neighbor analysis was performed by a modification of the procedure of Sgaramella and Khorana (Sgaramella, V., & Khorana, H. G. (1972) *J. Mol. Biol.* 72, 427444.). The product from incubation with [α-$^{32}$P]dCTP or [α-$^{32}$P]dGTP was isolated by gel electrophoresis and digested with micrococcal nuclease and spleen phosphodiesterase. The digestion mixture was then diluted with carrier nucleoside-3'-monophosphates, the mixture separated by HPLC, and the radioactivity determined by scintillation counting.

Polymerase reactions were performed following the method of Cobianchi and Wilson (Cobianchi, F., & Wilson, S. H. (1987) *Methods in Enzymology* 152, 94–110, Berger, S. L., Kimmel, A. R. (Eds.) Academic Press, New York.). Reaction with AMV reverse transcriptase was performed by the method of Larson et al. (Larson, K., Sahm, J., Shenkar, R. & Strauss, B. (1985) *Mutation Research* 150, 77–84.). Boehringer Mannheim and Pharmacia both provided Klenow fragment of DNA polymerase (1 U/mL). Polynucleotide kinase was from Pharmacia. T7 RNA polymerase, AMV reverse transcriptase, and T4 DNA polymerase were from Pharmacia. In previous experiments, the Klenow fragment of DNA polymerase I was used to enzymatically prepare oligonucleotides including non-standard bases. Additionally, in previous experiments, radiolabeled nucleoside triphosphates, including $^3$H and $^{32}$P radiolabeled standard and non-standard bases were enzymatically incorporated into a oligonucleotide.

The DNA oligonucleotides containing only standard nucleobases were deprotected in conc. ammonia over night at 60° C. and purified. The DNA oligonucleotides containing the non-standard puDAA nucleobase were prepared analogously, except that the puDAA phosphoramidite was coupled with a reaction time of 3.0 min, the double of the time used for coupling of the standard nucleosides. These oligonucleotides were deprotected and released from the support by incubation with saturated ammonia in a water-ethanol (3:1) mixture for 3 h at RT followed by an additional 1 h at 50° C. The support was removed by centrifugation, and the ammonia solution removed by rotary evaporation (30–40° C.) using a dry ice/2-propanol cold trap.

The oligonucleotides were HPLC-purified using the "trityl on" procedure (Supelco, LC18-S, length 25 cm, diameter 10 mm, particle size 5 μm; elution solvents: A: 0.1 M TEAA pH 7.0/Me—CN 99:1, B: 0.1 M TEAA pH 7.0/Me—CN 60:40, C: Me—CN, D: 0.1 M TEAA pH 7.0/Me—CN 80:20; flow rate, 6.0 mL/min.; gradient see below; UV-detection at 260 nm). The product-containing fractions were combined, the solvent removed under high vacuum, and the residue twice taken up in water (2 mL) and lyophilized to remove all salts.

The product was detritylated by adding 80% HOAc (300 μL). EtOH (300 μL) was then added, and the solvents removed under high vacuum. The residue was taken up with water (1 mL), and the trityl alcohol removed by extracting three times with ether (1 mL). The oligonucleotides were then purified by "trityl off" HPLC. Product-containing fractions were combined and the solvents removed under vacuum. Finally the product was dissolved in water (2 mL) and then lyophilized. This step was repeated to remove all salts. The resulting product was dissolved in sterile water (0.5–1.0 mL) and quantified by UV-spectroscopy. All synthesized oligonucleotides were checked for purity by analytical HPLC.

Oligonucleotide sequences, solvent gradients (percentage of buffer B, C or D in A) during HPLC purification and corresponding retention times are given below:

OL-J1: GCT[puDAA]TCTCCCTATAGTGAGTC-GTATTA; gradient "trityl-on" 15–20% in 5' to 26% in 25' to 40% in 5' (buffer C), $t_R$ 23'; gradient "trityl-off" 45–55% in 30' (buffer D), $t_R$ 12'.

OL-J2: GCC[puDAA]TCTCCCTATAGTGAGTC-GTATTA; gradient "trityl-on" 40–50% in 5' to 57% in 25' to 100% in 5' (buffer B), $t_R$ 21'; gradient "trityl-off" 45–58% in 30' (buffer D), $t_R$ 12'.

OL-J3: GCT[puDAA]CCTCCCTATAGTGAGTC-GTATTA; gradient "trityl-on" 40–50% in 5' to 55% in 25' to 100% in 5' (buffer B), $t_R$ 18'; gradient "trityl-off" 45–50% in 25' to 70% in 5' (buffer D), $t_R$ 14'.

OL-J4: GCC[puDAA]CCTCCCTATAGTGAGTC-GTATTA; gradient "trityl-on" like for OL-J1, $t_R$ 21'; gradient "trityl-off" 45–50% in 25' (buffer D), $t_R$ 12'.

OL-J5: TCGG[puDAA]TCCG; gradient "trityl-on" 40–50% in 10' to 60% in 25' to 100% in 5' (buffer B), $t_R$ 30'; gradient "trityl-off" isocratic 39% buffer D, $t_R$ 10'.

OL-J6: TrT[puDAA]TCCG; gradient "trityl-on" 40–50% in 5' to 90% in 25' (buffer B), $t_R$ 23'; gradient "trityl-off" 5–20% in 30' (buffer C) [purified on an analytical otherwise identical column; flow 1 mL/min.], $t_R$ 21'.

Characterization of puDAA containing oligodeoxyribonucleotides. A small aliquot (ca. 0.2 O.D. at 254 nm) of the oligonucleotide was dissolved in digestion buffer (0.7 mL) and incubated with phosphodiesterase (5 μg) at 37° C. for 30 min. Alkaline phosphatase (5 μg) was added and the reaction continued for 30 min. at 37° C. The relative nucleotide composition was determined by HPLC analysis of aliqouts of the digestion mixture (Column: Supelco, LC18-S analyt., length 25 cm, diameter 4.6 mm, particle size 5 μm; elution solvents: A: 0.05 M K$_2$HPO$_4$ pH 7.0, B: 0.05 M K$_2$HPO$_4$ pH 7.0/MeOH=60:40; flow rate: 1.0 mL/min.; gradient: 0% B 10 min., to 60% B in 18 min., then at 60% B for 7 min.; UV-detection at 260 nm; $t_R$ [min.]: d[puDAA] 15.4; dC, 16.2; T 26.1; dG 27.3; dA 30.9). The following absorption coefficients (260 nm) were used: d[puDAA] 7500, dC, 7300, dA 15400, T 8800, dG 11700 [47]. The identity of the d[puDAA] signal was demonstrated by coinjection of synthetical d[puDAA].

Enzymatic oligoribonucleotide synthesis using T4 RNA ligase. General protocol: Water (2.0 μL), ligation buffer (5.0

μL), RNA acceptor (1.0 μL, 1.0 mM) and ribonucleoside bisphosphate (1.0 μL, 2.0 mM) were mixed and an aliquot of the reaction mixture removed for HPLC analysis. T4 RNA ligase (1.0 μL, 20 U) was added and the reaction incubated for 4–6 h at 37° C. under HPLC control of aliquots of the reaction mixture. Alkaline phosphatase was added directly to the reaction mixture and the resulting solution again incubated for 45 min. at 37° C. The reaction mixture was diluted to 500 μL, microfiltrated and the product isolated by HPLC (Column: Supelco, LC18-S-analyt., length 25 cm, diameter 4.6 mm, particle size 5 μm; elution solvents: A: 0.1 M TEAA pH 7.0, B: pure Me—CN; flow rate: 1.0 mL/min.: gradient; 5–11% B in A in 34 min.; UV-detection at 260 nm, for pyADD at 360 nm). Product containing fractions were pooled and lyophilized. For removal of the volatile buffer salts the product was twice dissolved in water and again lyophilized. The RNA product was quantified by UV-spectroscopy, dissolved in the appropriate amount of sterilized water and then used for the next reaction cycle. In early reactions, the reaction volumes were up to 10 fold higher; the same relative concentration of all components was used, however.

Calculated $\epsilon$ at 260 nm and results of HPLC and UV analysis: CGGA: $\epsilon$ 46100; $t_R$ [min.] 19.8; CGGA[pyDAA]: $\epsilon$ 49400; $t_R$ [min.] 25.3; yield 48%; A(260 nm)/A(360 nm) 3.8; CGGA[pyDAA]A: $\epsilon$ 64800; $t_R$ [min.] 29.0; yield 40%; A(260 nm)/A(360 nm) 4.6; CGGA[pyDAA]AA: $\epsilon$ 80200; $t_R$ [min.] 30.7; yield 46%; A(260 nm)/A(360 nm) 5.6; CGGA [pyDAA]AAA: $\epsilon$ 95600; $t_R$ [min.] 31.8; yield 31%; A(260 nm)/A(360 nm) 6.5. For the calculation of $\epsilon$ the extinction coefficients of the deoxyribonucleosides were used (see above). The $\epsilon$ of pyDAA (3300 at 260 nm; 10000 at 360 nm) was from a model compound containing the pyrazine heterocycle. The final yield of RNA octamer was 1.5 mmol.

Characterization of pyADD containing oligoribonucleotides. The synthesized penta and hexaribonucleotide were digested to the ribonucleosides and analyzed by HPLC as described above for the oligodeoxyribonucleotides (Column: Supelco, LC18-S-analyt., length 25 cm, diameter 4.6 mm, particle size 5 μm; elution solvents: A: 0.05 M $K_2HPO_4$ pH 7.0, B: 0.05 M $K_2HPO_4$ pH 7.0/MeOH=80:20: flow rate: 1.0 mL/min.; gradient: 0% B 3 min., to 100% B in 14 min., then at 100% B for 8 min.; UV-detection at 260 nm, for pyADD at 360 nm). $\epsilon$ values see above. Detection at 360 nm was used for quantification of pyADD and the identity of the pyADD peak was confirmed by coinjection with synthetical pyADD ribonucleoside.

Deprotection and purification of oligoribonucleotides containing standard nucleotides only. Two RNA octamers were purchased from MWG-Biotech in their 5'-O-DMT- and 2'-O-Fpmp-protected form. Following the instructions of the manufacturer, the oligonucleotides were deprotected by incubation in the provided deprotection soln. (500 μL, pH 2–3) for 24 h at RT. The soln. was cooled to 0° C., neutralized with $Et_3N$ (60 μL) and microfiltrated prior to HPLC purification, which was performed as described above for the pyADD containing octaribonucleotides.

In vitro transcription using T7 RNA polymerase. Water (3 μL), TMS-buffer (4.0 μL; 200 mM TrisHCl, 100 MM $MgC_2$, 5 mM spermidine), DTT soln. (1.0 μL; 100 mM), RNAse inhibitor (1.0 μL), NTPs (5.0 μL; 1:1:1:1, 10 mM/NTP), Triton X-100 soln. (1.0 μL; 0.2%), DNA template (1.0 μL; 27 pmol), BSA soln. (1.0 μL; 1 mg/mL), $\gamma$-$^{32}$P-GTP (1.0 μL; 1 μCi) and T7 RNA polymerase (2 μL, 140 U) were incubated at 37° C. for 20 min. To stop the reaction, stop buffer (12 μL) was added and the resulting mixture heated to 67° C. for 3 min. The reaction mixture was separated on a denaturing 20% polyacrylamide gel, and the products analyzed by autoradiography using a phosphor imager.

What is claimed is:

1. A method of making an oligonucleotide, the method comprising:

providing a template oligonucleotide comprising a sequence of nucleotides, the template comprising at least one non-standard nucleotide at a preselected site in the sequence;

contacting the template with a mixture of nucleotide triphosphates, the mixture comprising nucleotide aiphosphates that are complementary to the nucleotides of the template, wherein the nucleotide triphosphate complementary to the non-standard nucleotide at the preselected site comprises a detivatized nucleotide; and forming an oligonucleotide complementary to a portion of the template by enzymatic polymerization of the nucleotide triphosphates in a sequence complementary to the portion of the template, wherein the non-standard nucleotide at the preselected site is iso-G or iso-C.

2. A method of making an oligonucleotide, the method comprising:

providing a template oligonucleotide comprising a sequence of nucleotides, the template comprising at least one non-standard nucleotide at a preselected site in the sequence;

contacting the template with a mixture of nucleotide triphosphates, the mixture comprising nucleotide triphosphates that are complementary to the nucleotides of the template, wherein the nucleotide triphosphate complementary to the non-standard nucleotide at the preselected site comprises a derivatized nucleotide; and forming an oligonucleotide complementary to a portion of the template by enzymatic polymerization of the nucleotide triphosphates in a sequence complementary to the portion of the template, wherein the enzymatic polymerization is performed with a polymerase selected from the group consisting of AMV reverse transcriptase, and Klenow fragment of DNA polymerase I.

3. The method of claim 2, wherein the polymerase is Klenow fragment of DNA polymerase I.

4. A method of making an oligonucleotide, the method comprising:

providing a template oligonucleotide comprising a sequence of nucleotides, the template comprising at least one non-standard nucleotide at a preselected she in the sequence;

contacting the template with a mixture of nucleotide triphosphates, the mixture comprising nucleotide triphosphates that are complementary to the nucleotides of the template, wherein the nucleotide triphosphate complementary to the non-standard nucleotide at the preselected site comprises a derivatized nucleotide comprising a radiolabel; and forming an oligonucleotide complementary to a portion of the template by enzymatic polymerization of the nucleotide triphosphates in a sequence complementary to the portion of the template, wherein the enzymatic polymerization is performed with T7 RNA polymerase.

* * * * *